United States Patent [19]

Misaki et al.

[11] Patent Number: 4,549,205
[45] Date of Patent: Oct. 22, 1985

[54] AMPOULE INSPECTING METHOD

[75] Inventors: Yoshiki Misaki, Ashiya; Seiji Owashi, Toyono, both of Japan

[73] Assignee: Takeda Chemical Industries, Ltd., Osaka, Japan

[21] Appl. No.: 491,533

[22] Filed: May 4, 1983

[30] Foreign Application Priority Data

May 10, 1982 [JP] Japan .................................. 57-77746
May 10, 1982 [JP] Japan .................................. 57-77747

[51] Int. Cl.$^4$ ........................ H04N 7/18; B07C 5/00; G01N 21/00
[52] U.S. Cl. .................................... 358/106; 209/939; 250/223 B; 356/240; 356/427
[58] Field of Search .................... 358/106; 250/223 B; 356/240, 427; 209/939

[56] References Cited

U.S. PATENT DOCUMENTS

| Re. 28,984 | 9/1976 | Drinkuth et al. | |
| 3,217,877 | 11/1965 | Honjyo et al. | |
| 3,576,442 | 4/1971 | Nakamura | 250/223 B |
| 3,598,907 | 8/1971 | Drinkuth | 358/106 |
| 3,775,556 | 11/1973 | Nagamatsu | 358/106 |
| 3,777,169 | 12/1973 | Walter | 358/106 |
| 3,942,042 | 1/1976 | Faani | 356/240 |
| 3,966,332 | 6/1976 | Knapp et al. | 356/197 |
| 4,087,184 | 5/1978 | Knapp et al. | 356/197 |
| 4,136,930 | 1/1979 | Gomm | 358/106 |
| 4,172,524 | 10/1979 | Holm et al. | 209/524 |

FOREIGN PATENT DOCUMENTS 2238156  2/1974  Fed. Rep. of Germany .

Primary Examiner—Howard W. Britton
Attorney, Agent, or Firm—Wenderoth, Lind & Ponack

[57] ABSTRACT

A method for inspecting transparent or semitransparent, liquid-filled containers as to whether or not the liquid in each of the container contains foreign matters. The inspection is carried out by passing the container in front of a television camera while the liquid in each container undergoes a spiral motion as it passes through an inspection region, and processing video signals generated from the television camera by the use of a unique controlling circuit. With this controlling circuit, distinction can be made between signals indicative of the presence of foreign matters in the liquid and that indicative of the presence of external flaws on the container.

17 Claims, 30 Drawing Figures

Fig. 2
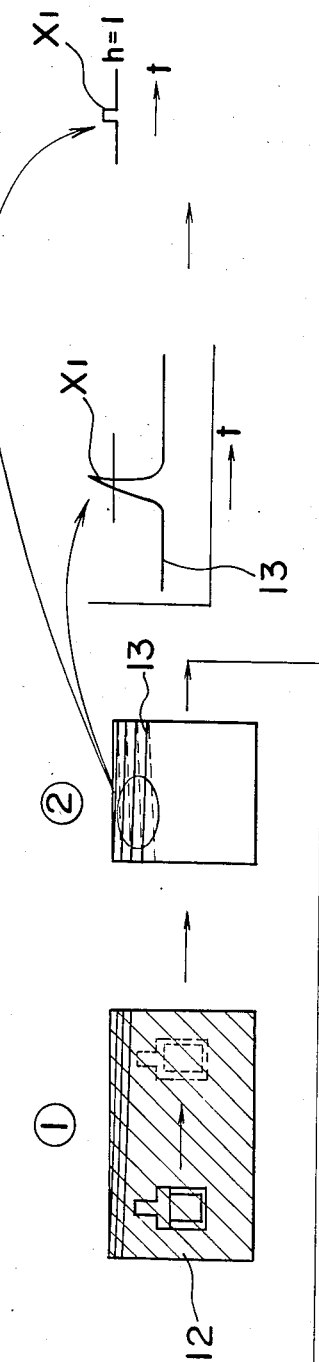
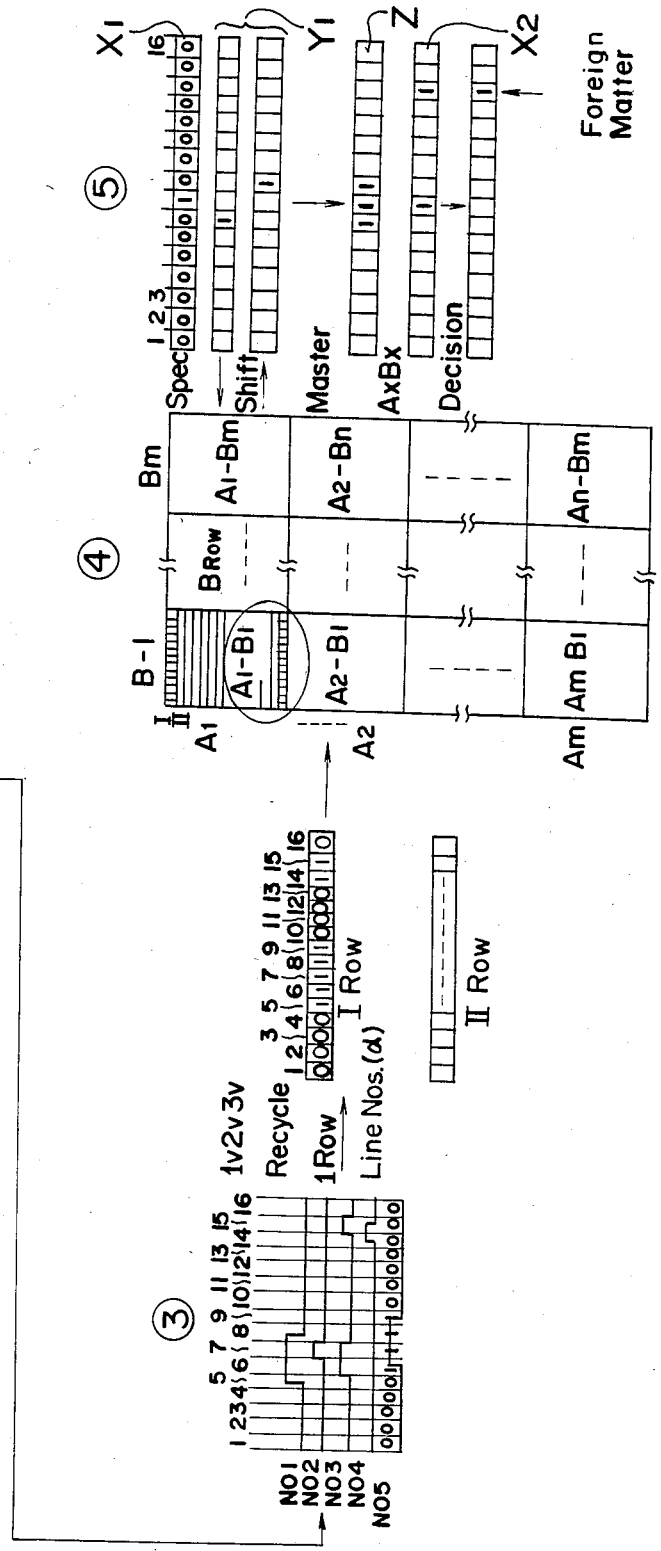

Fig. 4 (I)
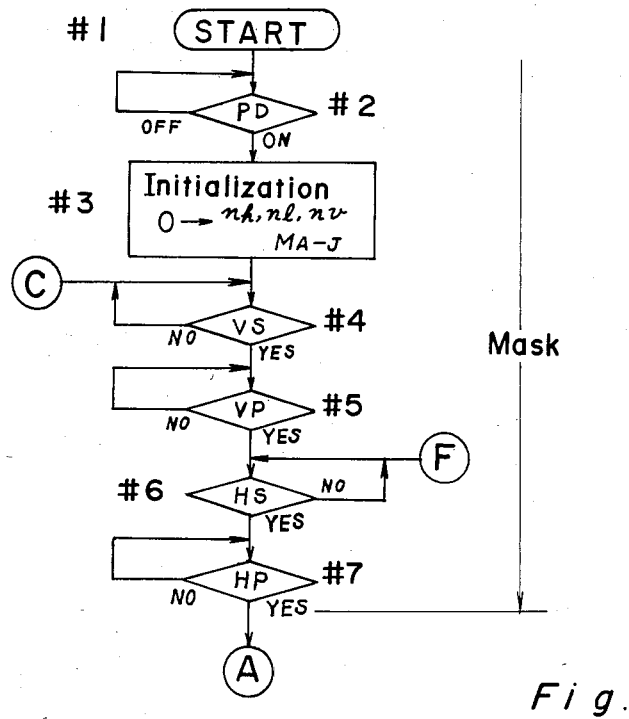
Fig. 4 (IV)
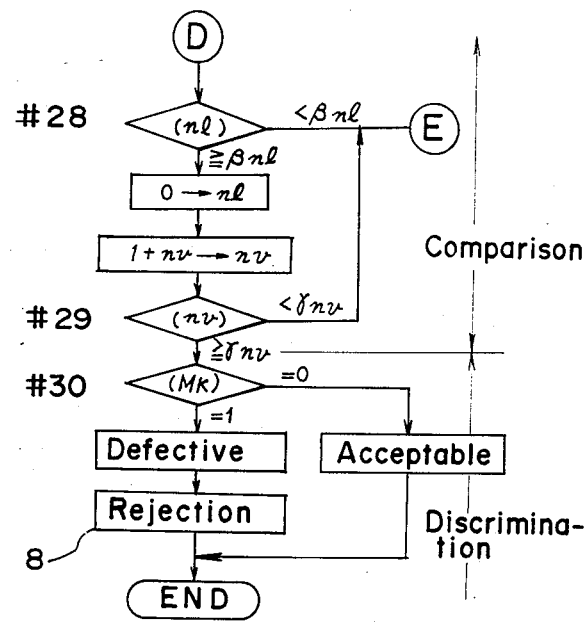

Fig. 4 (II)
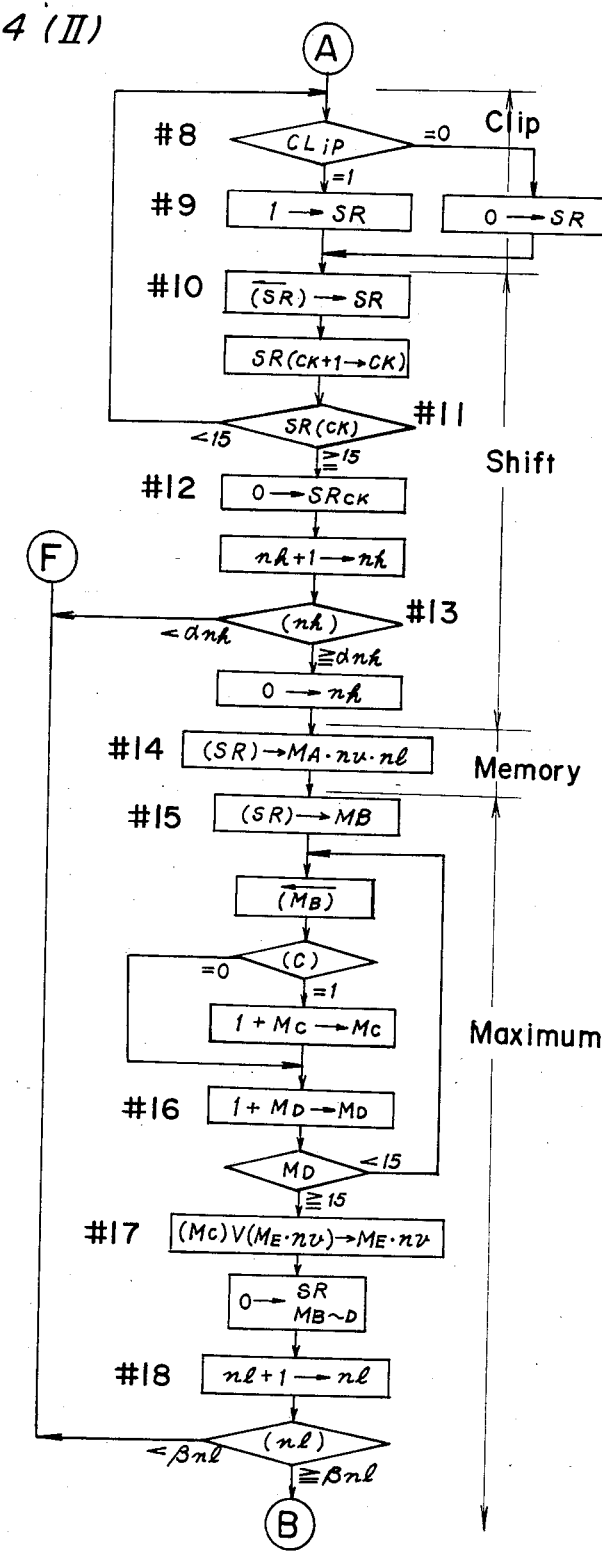

Fig. 4 (III)
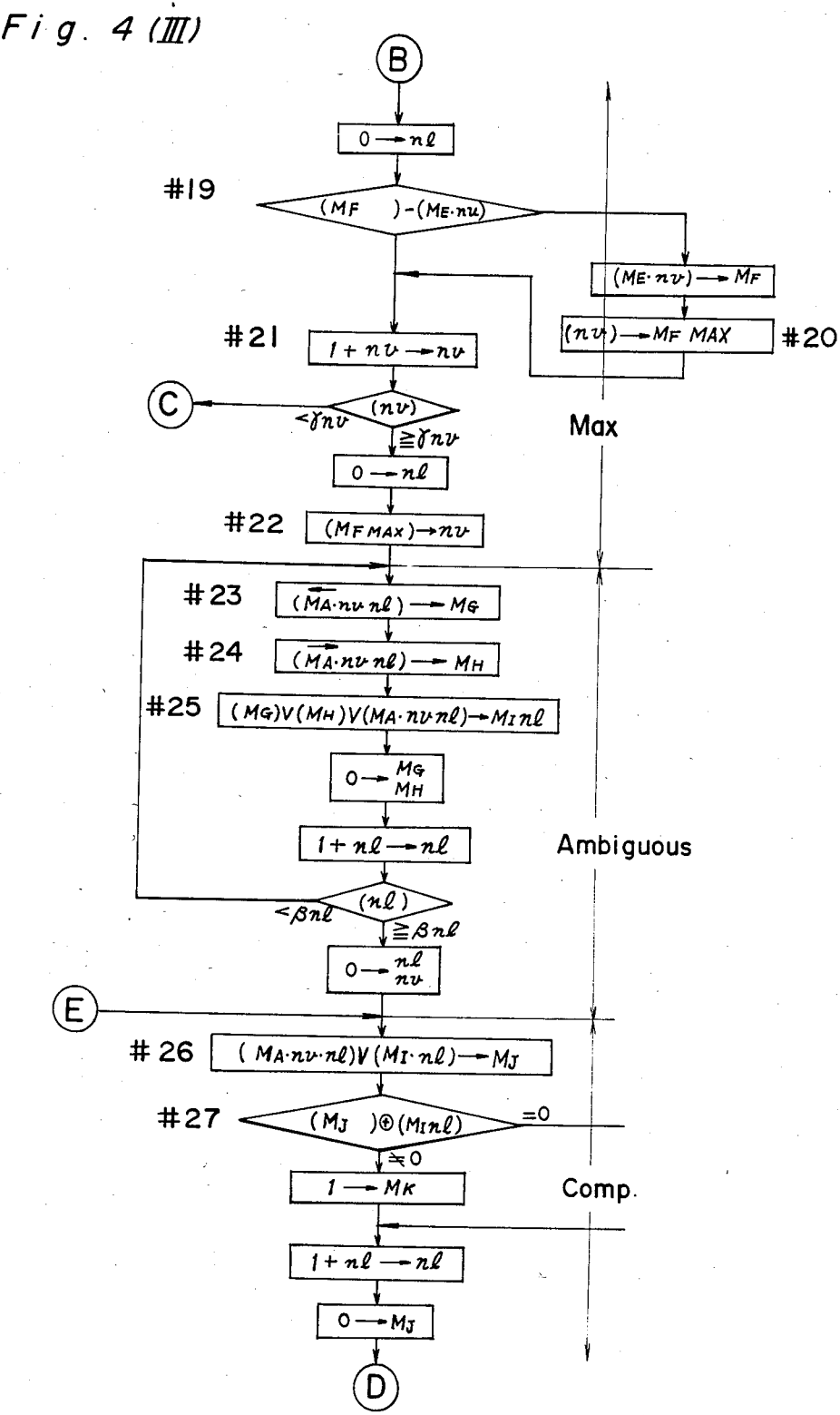

Fig. 7 (I)
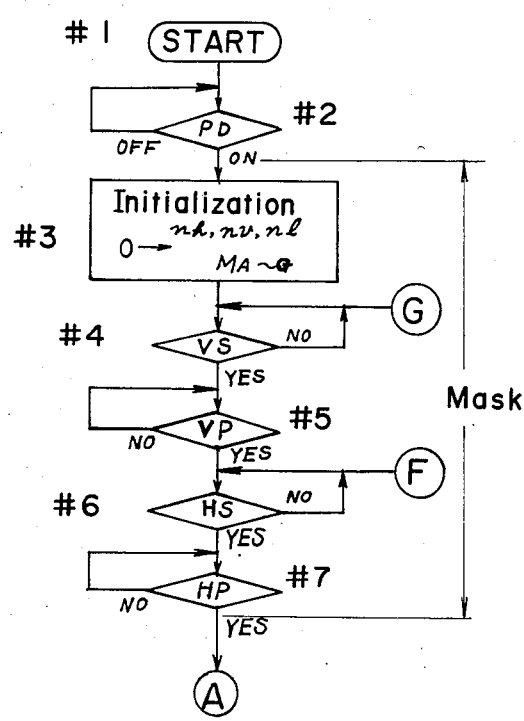
Fig. 7 (IV)
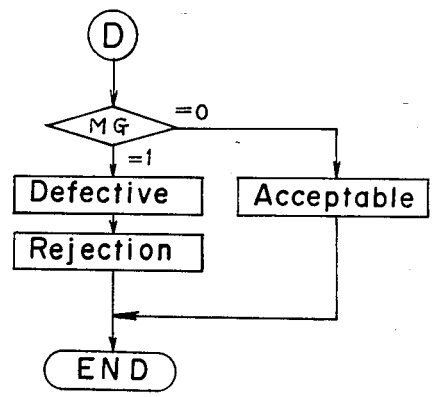

Fig. 7(III)
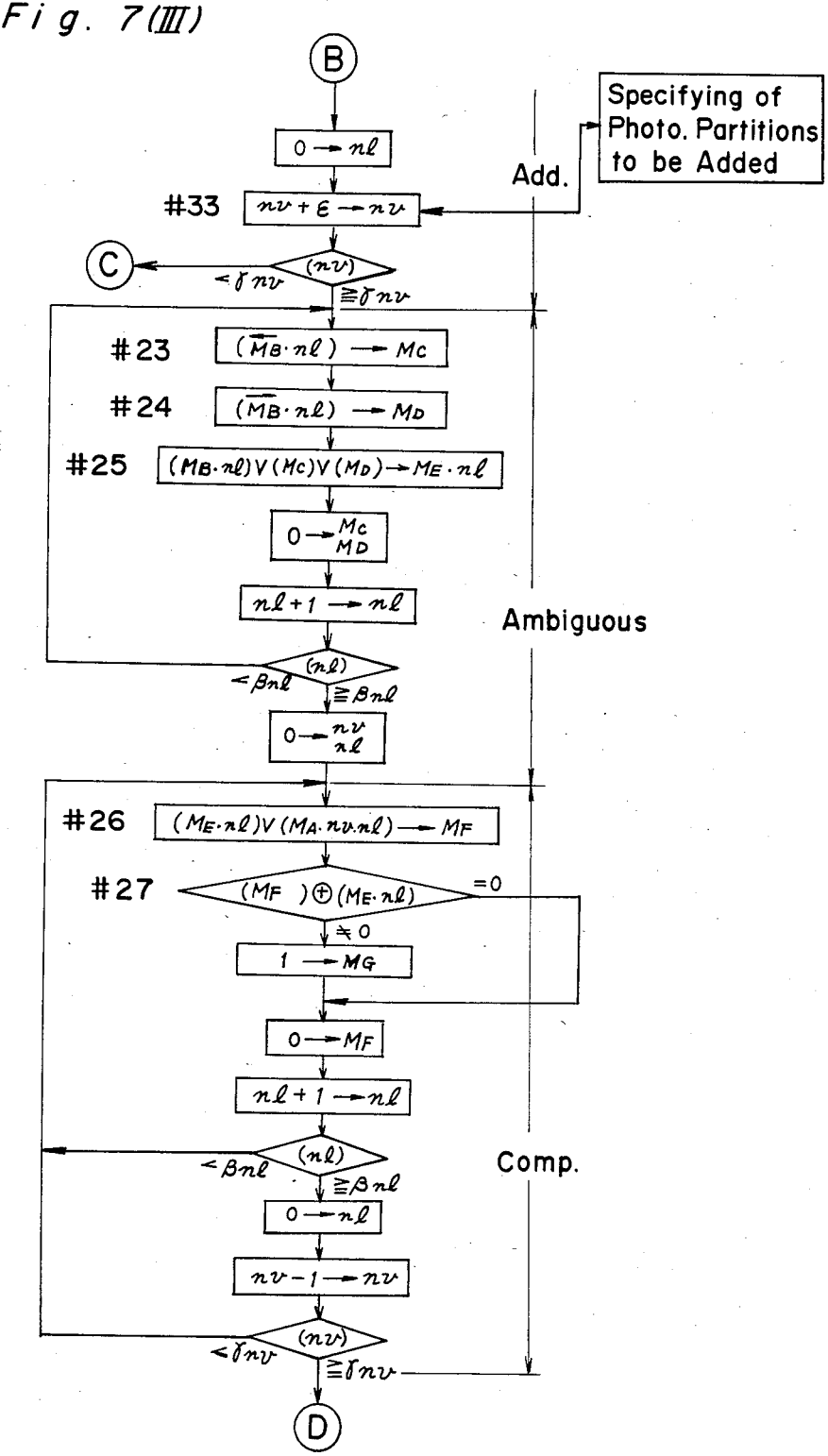

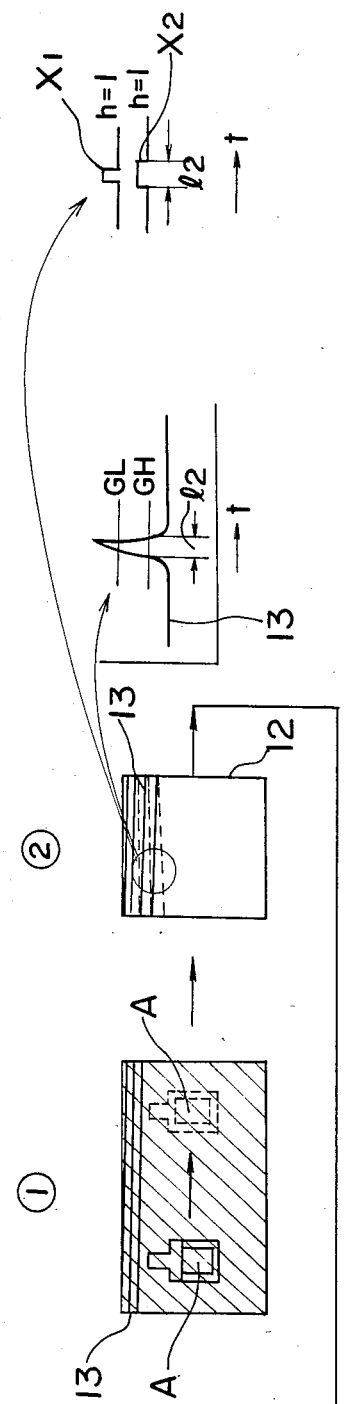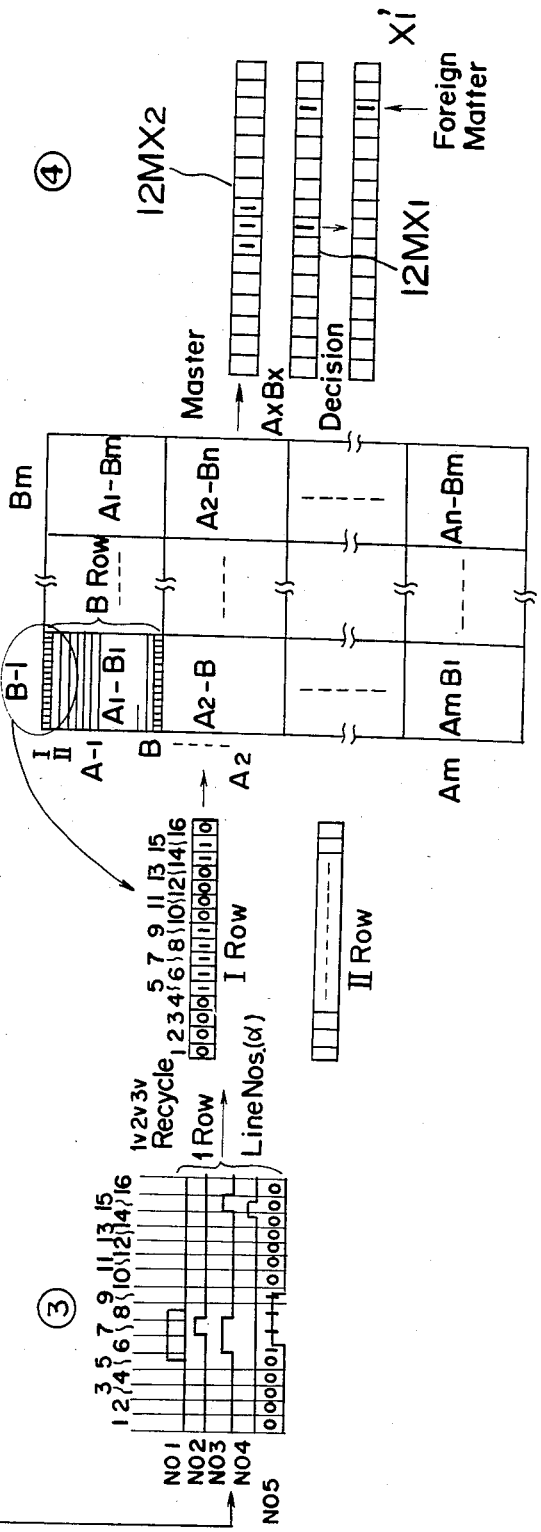
Fig. 8

Fig. 10 (I)
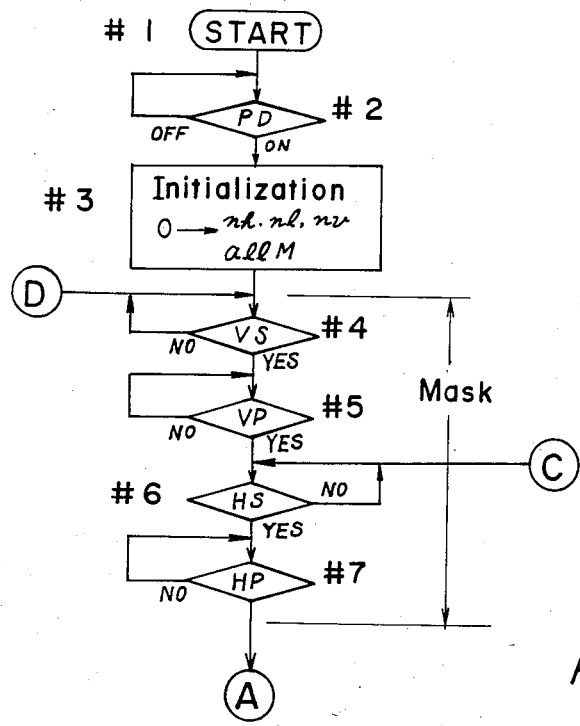
Fig. 10 (IV)
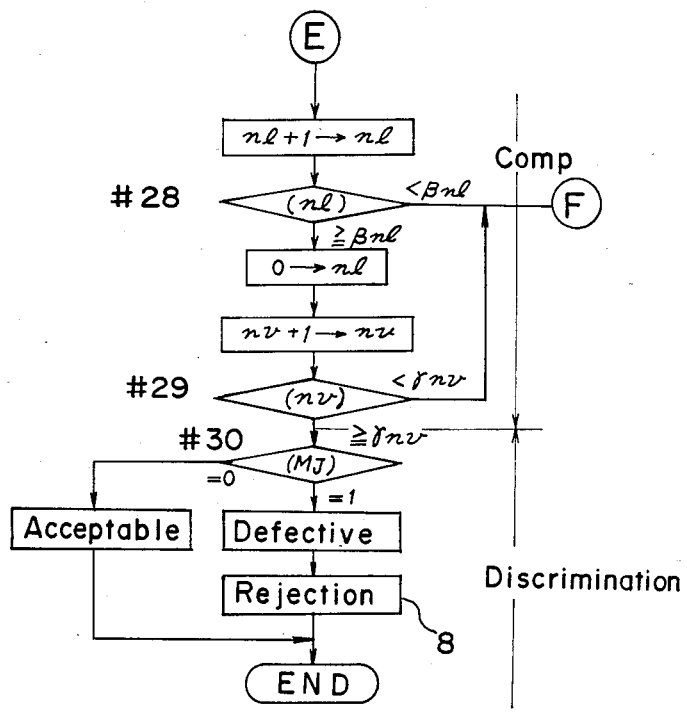

Fig. 10 (II)
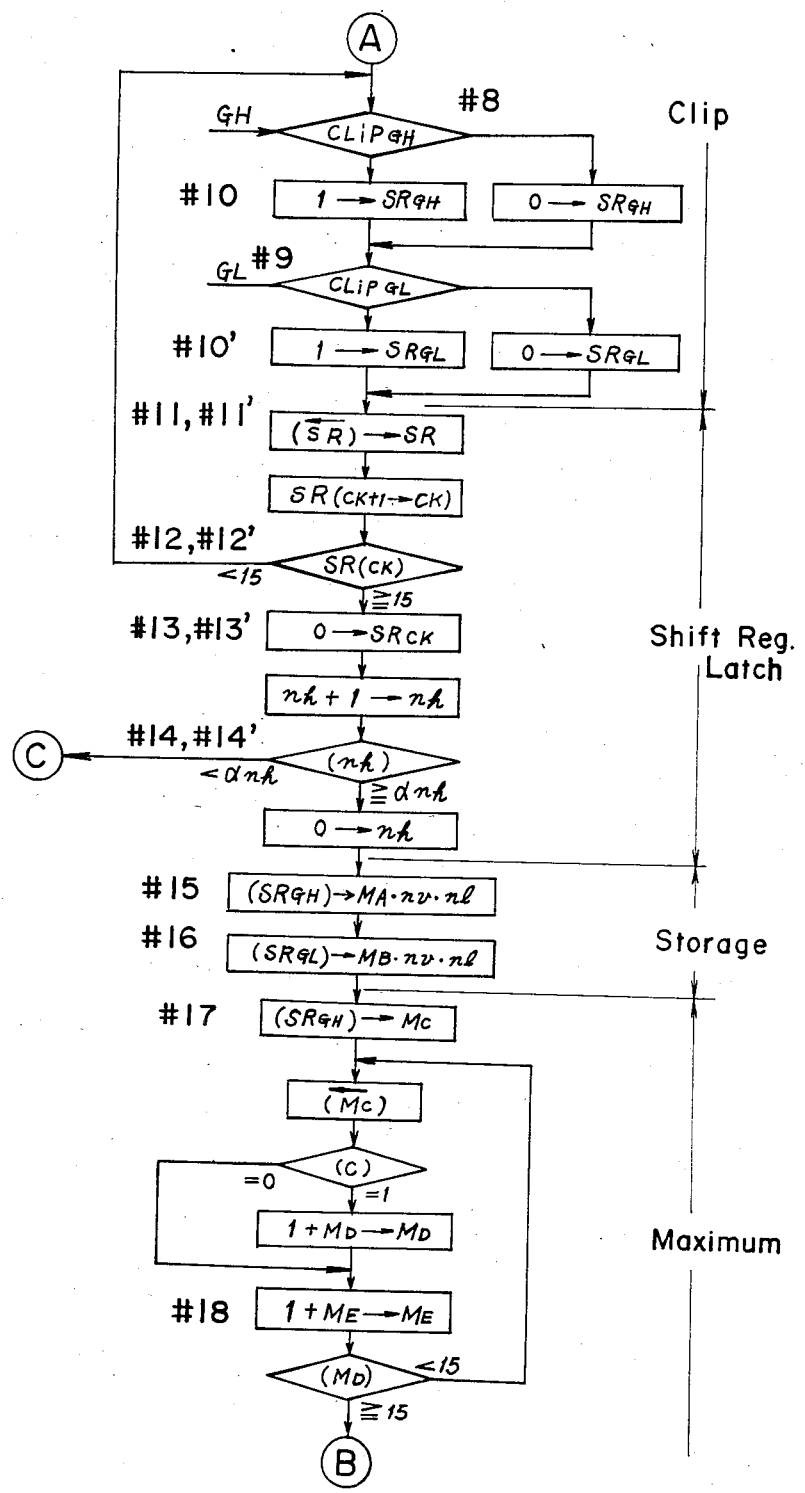

Fig. 10 (III)
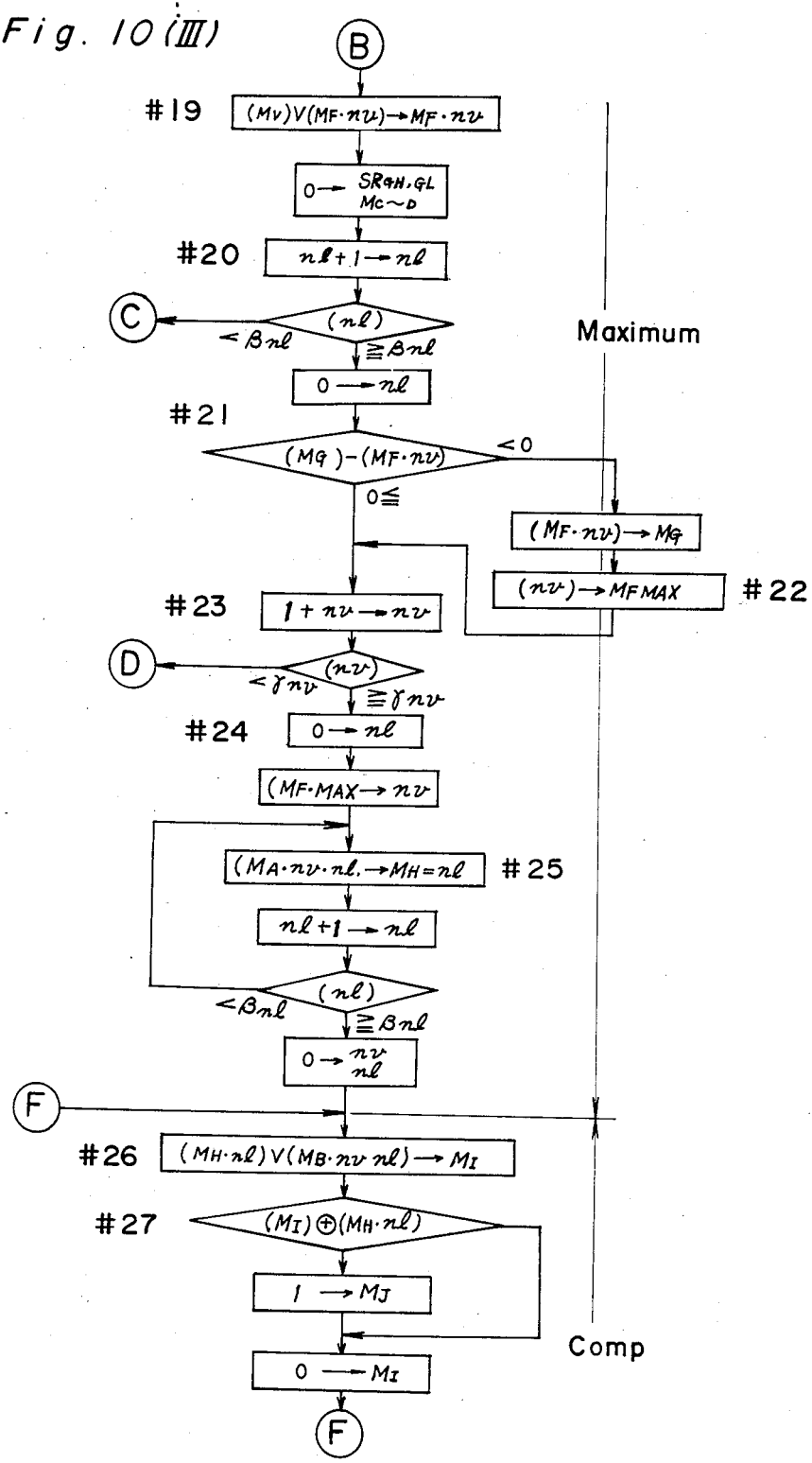

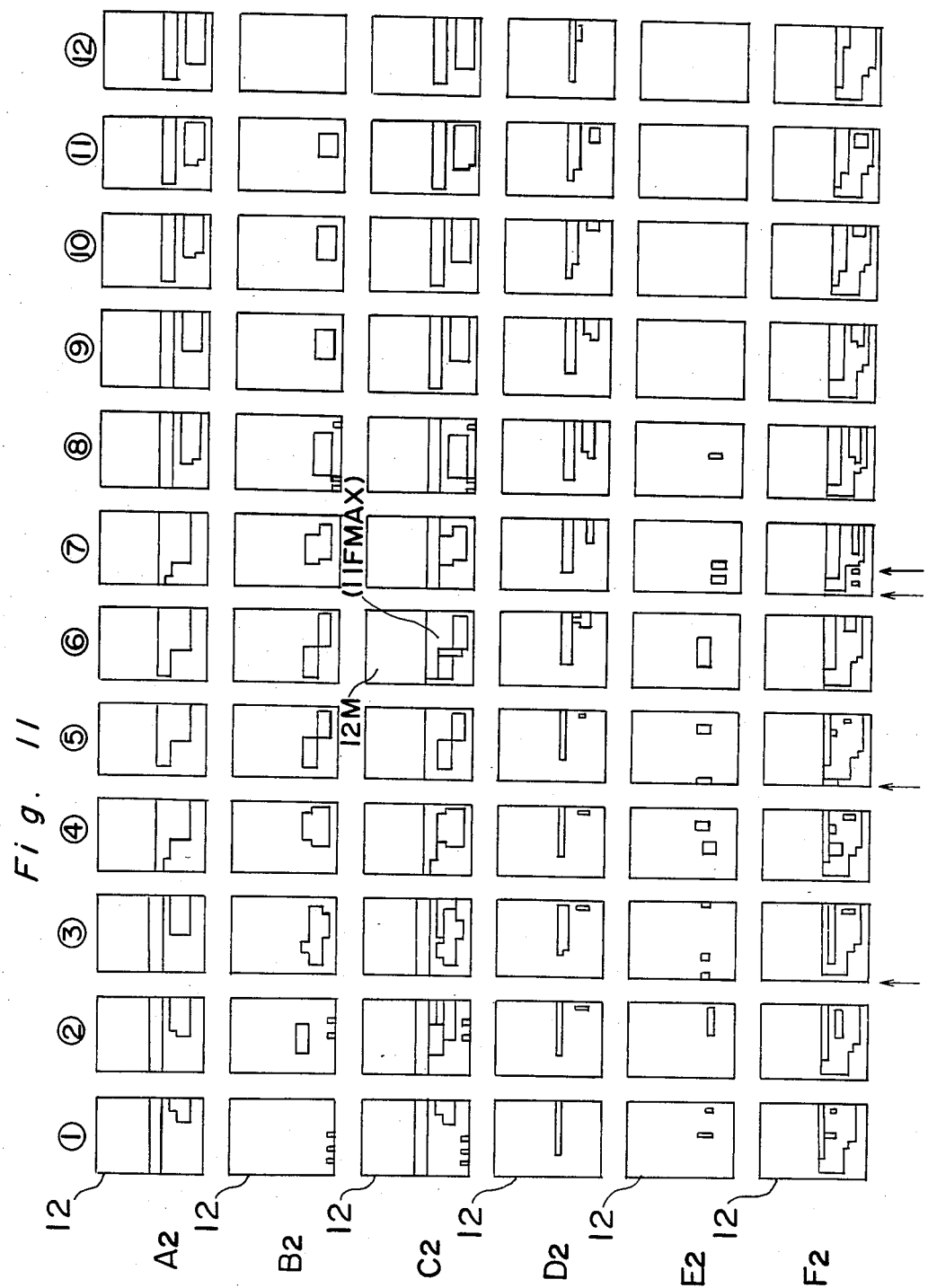

Fig. 13 (I)
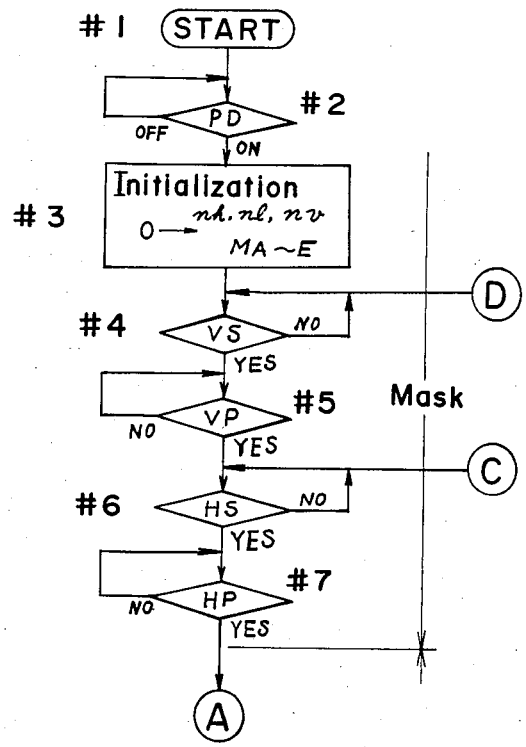
Fig. 13 (IV)
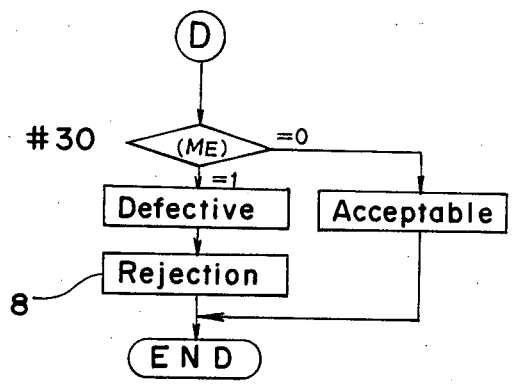

Fig. 13 (II)
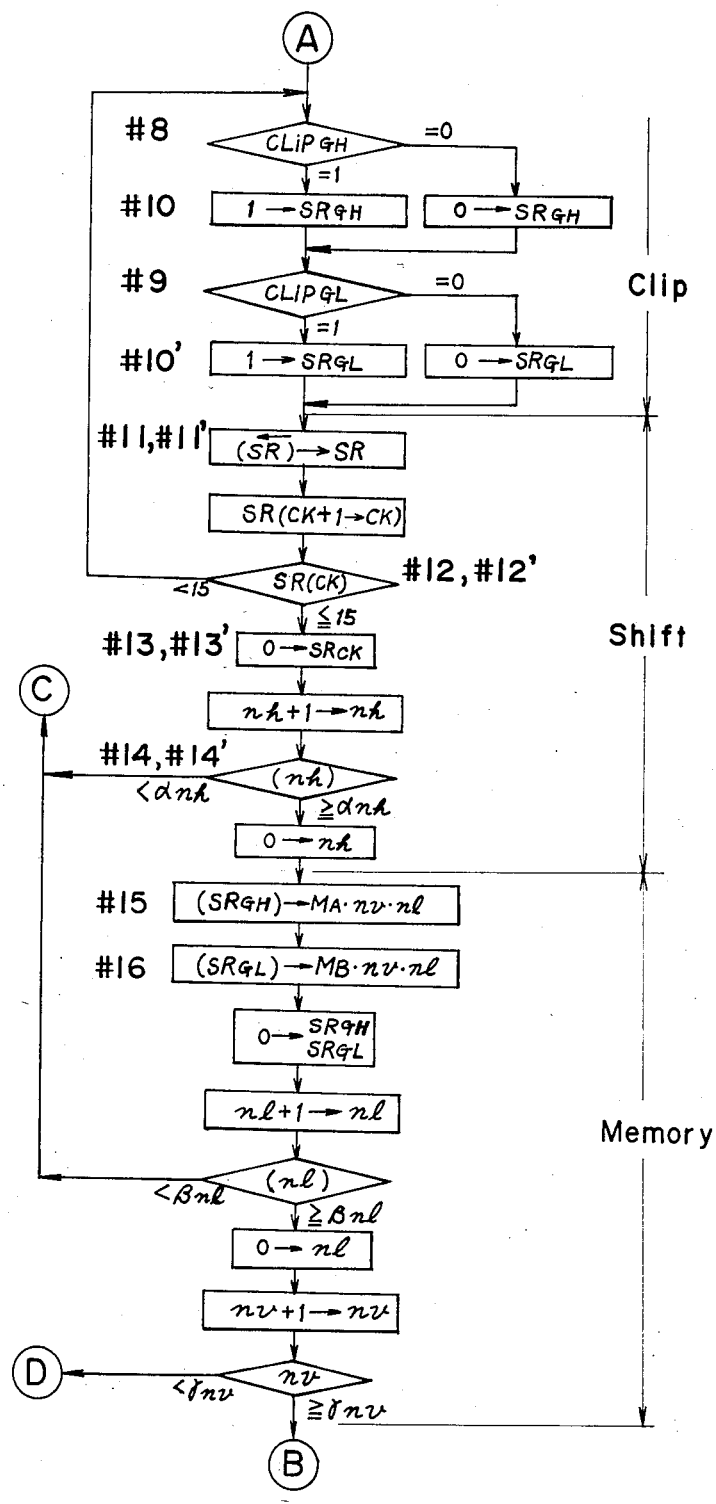

Fig. 13 (III)
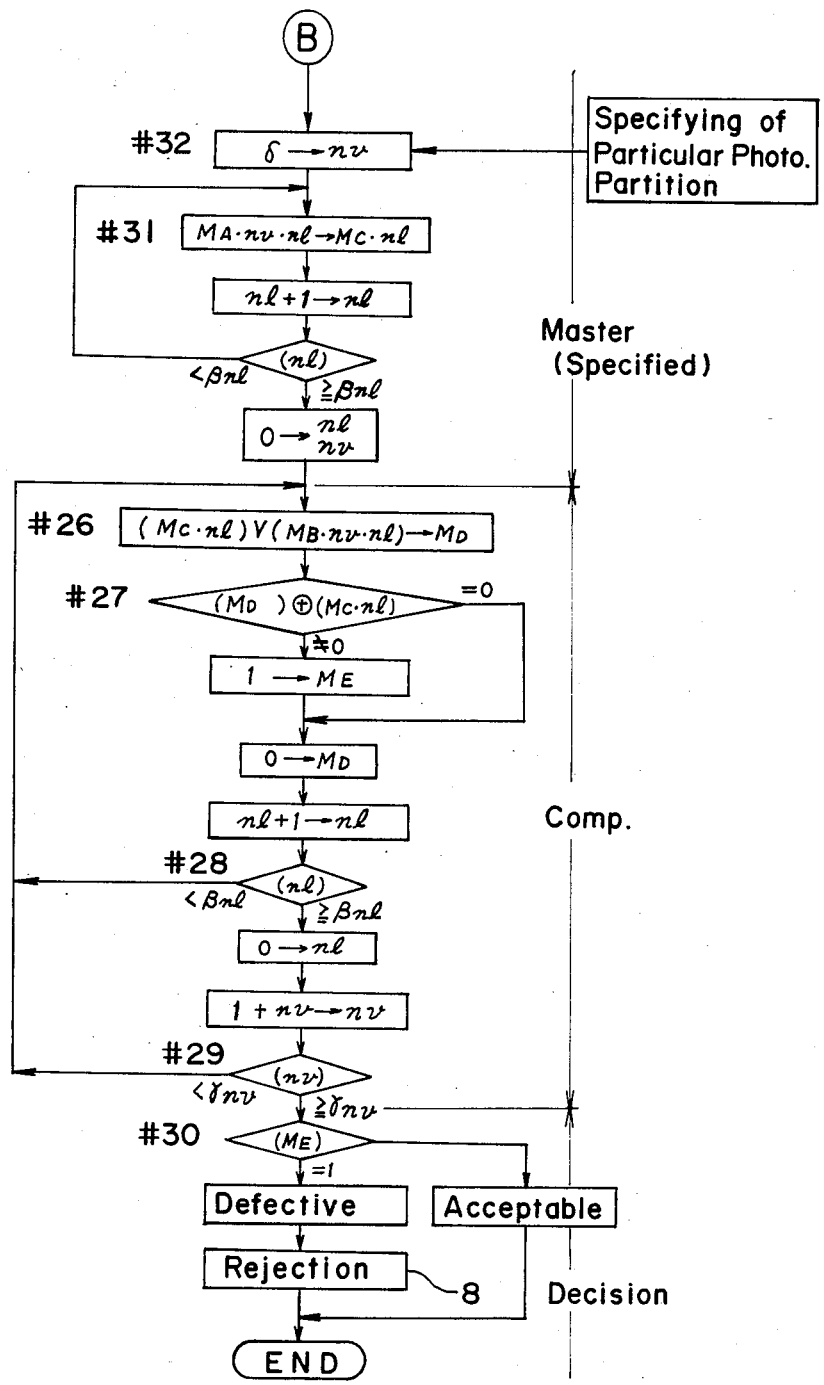

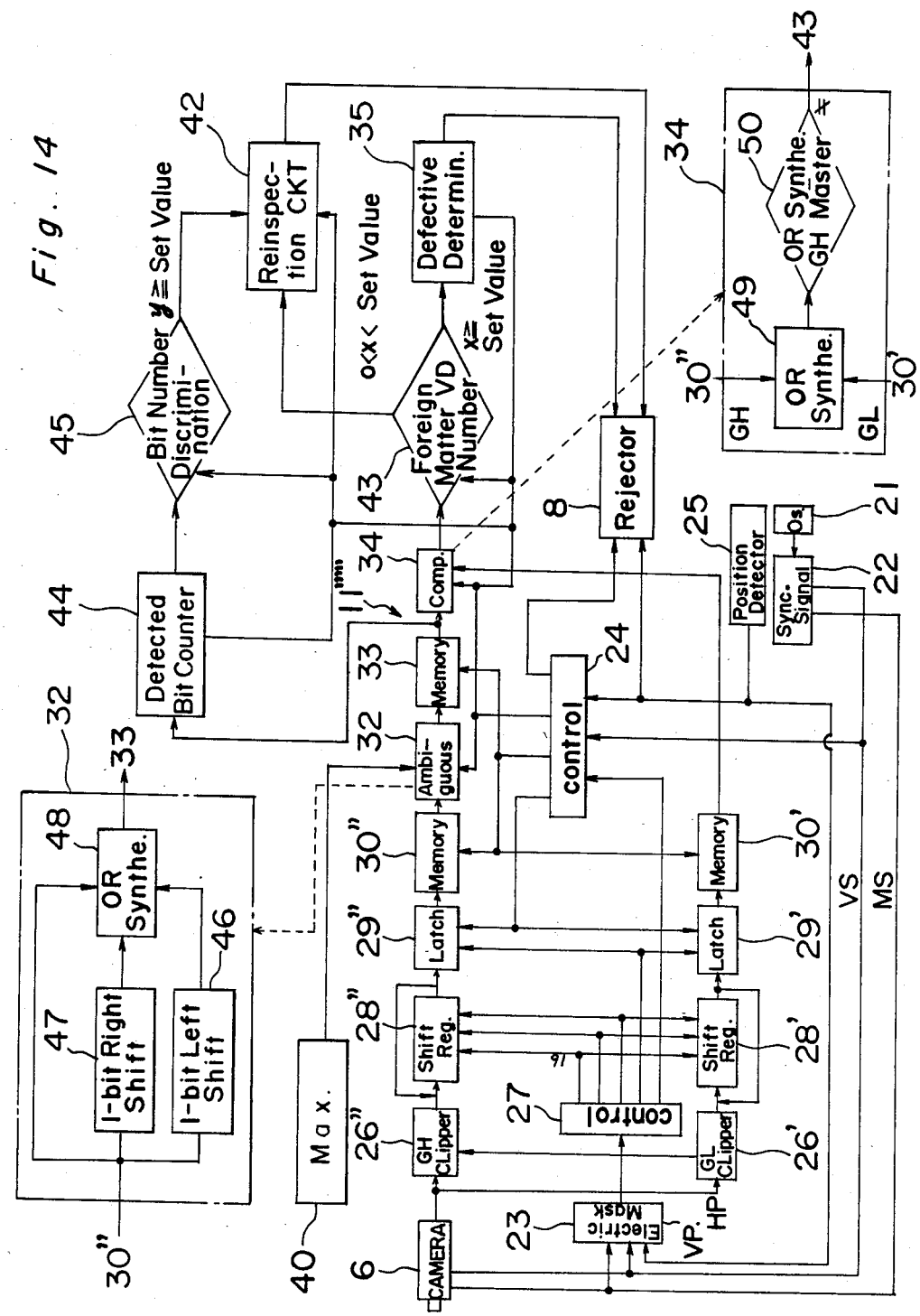

Fig. 15 (III)
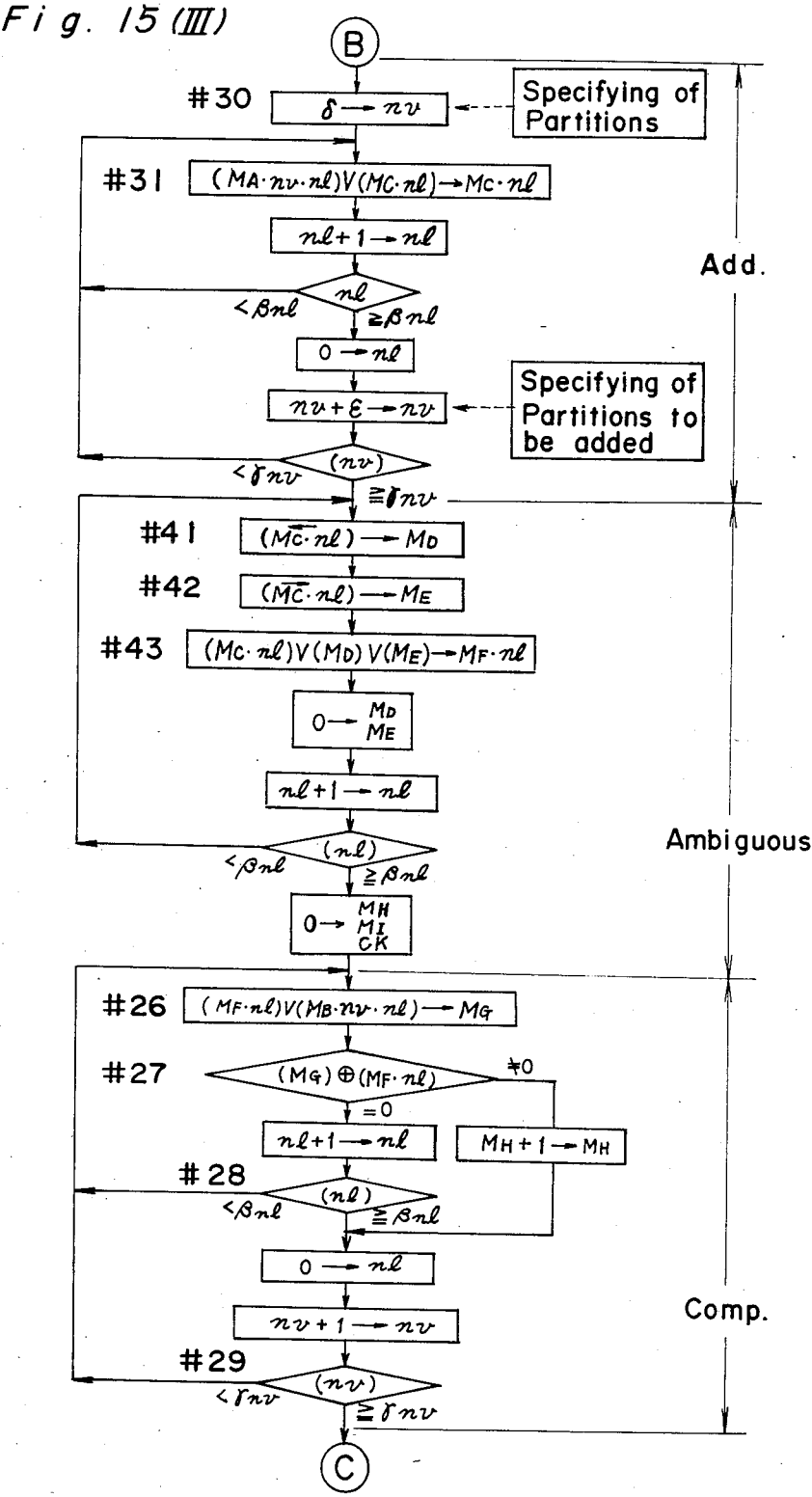

Fig. 15 (IV)
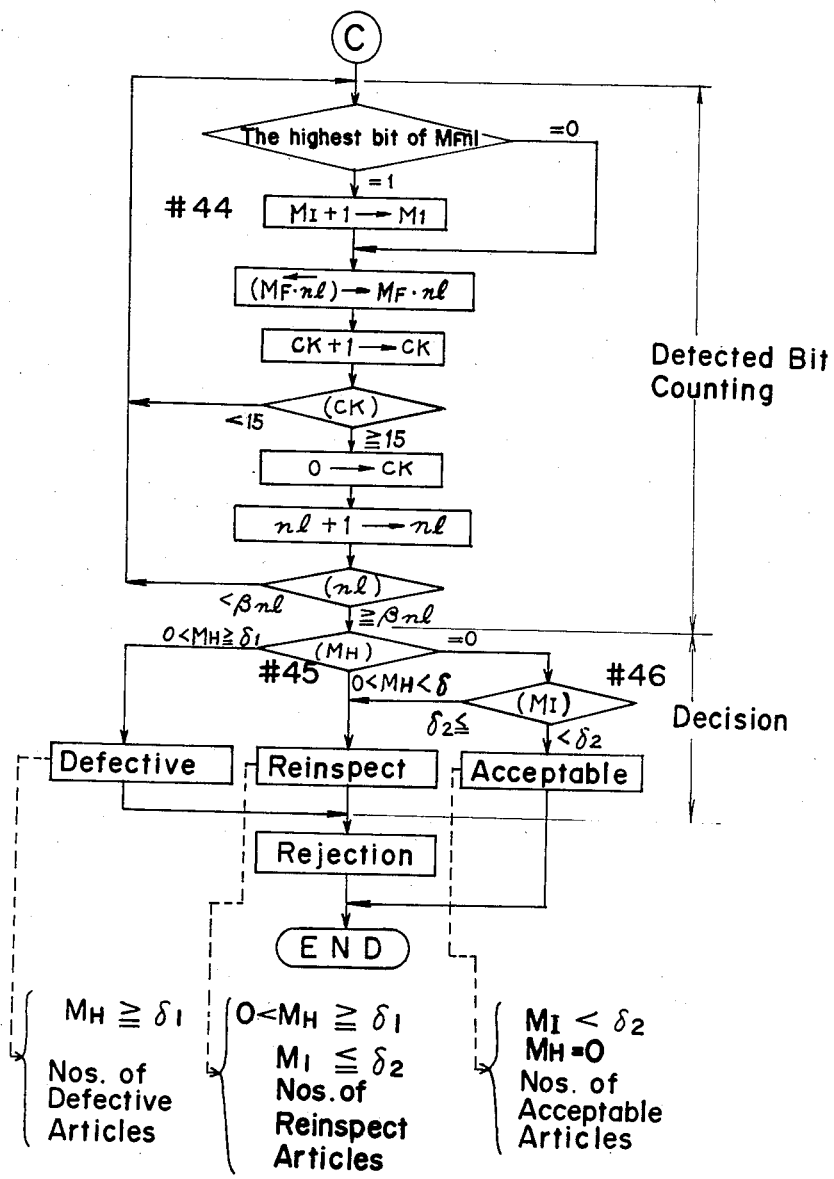

AMPOULE INSPECTING METHOD

The present invention relates to a method of automatically inspecting transparent or translucent liquid-filled containers such as ampoules or vials and, more particularly, to a method of automatically inspecting such containers by the use of a television camera as to the existence of foreign matters in the sealed containers with medical fluid contained therein.

Conventional inspection of articles, such as ampoules, by the use of a television camera as to the presence or absence of foreign matters in such articles has been carried out such as disclosed in, for example, the U.S. Pat. No. 3,576,442. However, according to the conventional method of this type, the foreign matters contained in the fluid contents filled in the sealed container, and the flaws the container itself has, have been considered completely the same with no distinction made therebetween so that their existence might be taken for abnormal voltage signals by the use of the television camera. Thus, the minute flaws a container has on its surface was mistaken for the foreign matters contained in the fluid contents to be detected, as the foreign matters became microbic. When they were detected at the same time, the detection accuracy of the foreign matters contained in the fluid contents became inferior. Accordingly, when a container, which has no foreign matters in the fluid contents, but has minute flaws on its surface, is detected, it is often regarded as having foreign matters in its fluid contents and is therefore distinguished as a defective one. Accordingly, there is such a disadvantage in that the number of articles detected as defective ones tends to increase.

To remove the disadvantages in the above-described conventional method, the present invention provides a method of inspecting fluid-filled, transparent or translucent sealed containers, capable of distinguishing the minute flaws in each of the containers from both the minute flaws, indistinguishable from the actual minute flaws, and the foreign matters in the fluid to be detected, and of detecting only the foreign matters with high accuracy.

According to the present invention, the containers to be inspected are caused to pass at approximately constant speed before a television camera provided in a stationary position. From the image signals of the photograph partitions of the container provided through the scanning operation by a television camera at three positions or more of the container, the detection signals indicative of the presence of foreign matter can be provided by processing them, thus allowing this type of inspection to be automatically and continuously performed.

Also, according to the present invention, the containers to be inspected are caused to pass at approximately constant speed before a television camera provided in a stationary position so as to simultaneously obtaining a first abnormal signal for detecting the foreign matter and a second abnormal signal corresponding to the minute flaws from among the image signals of the container provided through the scanning operation by a television camera at three positions or more of the container. Only the first abnormal signal, which has nothing to do with the second abnormal signal, can be provided by mutually processing them, thus allowing this type of inspection to be automatically and continuously performed.

Furthermore, according to the present invention, the first abnormal signal is fetched with a level as a reference, the level being low in sensitivity enough to detect the foreign matters from the image signals of a container provided through the scanning operation of the television camera and, simultaneously, the second abnormal signal is fetched with a level as a reference, the level being much higher in sensitivity than the above-described level, to remove the minute flaws, and the second abnormal signal in a particular photograph partition (or frame) where the second abnormal signals are maximum in number is compared with the first abnormal signal in the other photograph partition (or frame) to decide that it is a signal corresponding to the foreign matter only when the latter and the former exist in a different region. A signal to be generated in accordance with the minute flaw is positively distinguished from the signal corresponding to the foreign matter for the elimination of the signal caused in accordance with the minute flaw so that the first abnormal signal corresponding to the foreign matter in the other photograph partition may be extracted with high precision. Also, in this case, if a particular photograph partition where the second abnormal signal is provided and which is provided in a location where a container scanned by the television camera has little to do with the reflection of the illumination is selected, the detection error caused by the illumination of the container can be reduced to detect the first abnormal signal in the other photograph partition with high accuracy.

In addition, according to the present invention, a specified range including the specified position at which a second abnormal signal taken at the high sensitivity level from the image signal of the particular photograph partitions (or frames), and its vicinity after abnormal electric signals have been catched at high and low sensitivity levels from among the image signals of each photograph partition (or frame) is set up, and then, a second abnormal signal fetched at a high sensitivity level from the image signals in the particular photograph partition is compared with a first abnormal signal fetched at a level in sensitivity low enough to detect the foreign matters from the image signals in the other photograph partition, with the signal of the latter being fetched as an abnormal signal corresponding to the foreign matter only when the signal of the latter exists outside a particular region of a photograph partition where the signal of the former exists thereby to decide only by the abnormal signal that the foreign matter contained in the fluid contents exists.

Thus, the present invention uses, as an apparatus for detecting the presence of foreign matters contained in the fluid filled in a sealed ampoule with minute flaws provided therein, an apparatus composed of a mechanism for turning the fluid contained in the ampoule, a television camera provided in a fixed position for photographing an ampoule passing at a constant speed before the television camera within the inspection region, a mechanism for sequentially scanning an ampoule by the use of the television camera at at least three positions or more of the ampoule spaced a constant distance to catch the image signals of each of the photograph partitions so as to draw out a first abnormal signal as a reference with a level of sensitivity low enough to detect the foreign matter from each of the image signals of each photograph partition of the ampoule thereby to generate the sequential voltage signals, a controlling circuit for converting the abnormal signals into a logic "1"

signal in the corresponding address divided into a matrix of photograph partitions, a memory apparatus for respectively temporarily storing the voltage signals of the converted logic "1", a specifying circuit for comparing the photograph partitions with each other to select a specified partition, an ambiguous region specifying circuit for adding the logic "1" to the periphery of the logic "1" signal of a specific photograph partition specified by the specifying circuit, a memory apparatus for temporarily storing the voltage signal of the ambiguous region specifying circuit, a controlling apparatus for sequentially delivering a voltage signal stored in the memory apparatus, a logical operation circuit for drawing out the extended logic "1" signal in a specific photograph partition and the logic "1" signal in each of the other photograph partitions to combine the logic "1" signals of both signals to sequentially provide the logical sum of them for each of the corresponding addresses, and thereafter performing the calculation to provide the logical exclusive OR between the logical sum and the extended logic "1" signal of the second abnormal signal in the specific photograph partition to generate an elimination signal when the logic "1" signal wherein both signals mutually do not have given relationship to the operation value is provided, and a control synchronizing circuit for synchronizing the camera to the memory apparatus to send the two voltage signals to the logical operation circuit in correctly drawn out relation. This apparatus perform the method comprising the steps of passing the ampoule at almost a constant speed before the television camera provided at the fixed position within the inspection region while turning the fluid in the ampoule, sequentially scanning the ampoule by the use of the television camera, at at least three positions or more of the ampoule spaced a constant interval from each other to catch the image signals of each photograph partition, drawing out an abnormal signal as a reference with a level of a constant sensitivity sufficient to detect the foreign matters from each of the image signals, converting the abnormal signals respectively into the logic "1" signals in the corresponding addresses divided into the matrix of photograph partitions for the temporary storage thereof, comparing the photograph partitions with each other to optionally select a specific photograph partition including, for example, the largest number of logic "1" signals, adding the logic "1" signal to the specified range of the periphery of the logic "1" signal of the specified photograph partition to temporarily store it, drawing out the logic "1" signal of the extended abnormal signal in the specific photograph partition and the first abnormal signal in each of the other photograph partitions from the memory apparatus while synchronizing the camera with the output of the memory apparatus, sequentially providing the logical sum for each of the corresponding addresses of the logic "1" signals of both signals, thereafter performing a logical operation of providing the logical exclusive OR of the logical sum and the extended logic "1" signal in the specific photograph partition, and determining that the logic "1" signal indicates the existence of the foreign matters in the fluid contents when the logic "1" signal comes to the digital operation value. Accordingly, the method of the present invention is higher in the practical value as an electric, automatic continuous inspection method of this type, since the foreign matters contained in the fluid except for the container flaws are adapted to be detected by a simple and positive electric method and, accordingly, the foreign matters in the fluid to be detected can be positively detected at a faster processing speed and with high sensitivity, separately from the minute flaws of the container, which are likely to be mistaken for the foreign matters if the shape of the foreign matters becomes microbic. This is because the method comprises the steps of stopping the container, turning the fluid, considering them as the images of a television camera secured to a given position, seeing the minute flaw the container has as an abnormal signal of a specified photograph partition and a fixed signal contained in its neighboring region, and comparing the fixed signal with the abnormal signal of each photograph partition to take the abnormal signal only of the latter, i.e., so-called floating signal for the abnormal signal of the foreign matter when the abnormal signal is drawn out from among the image signals to detect the presence of the foreign matter.

Moreover, the present invention uses, as an apparatus for electrically detecting the existence of foreign matters contained in the fluid filled in a sealed ampoule with minute flaws provided therein, an apparatus composed of a mechanism for turning the fluid contained in the ampoule, a television camera provided in a fixed position for photographing an ampoule passing at almost a constant speed before the television camera within the inspection region, a mechanism for sequentially scanning the ampoule by the use of the television camera at at least three positions or more of the ampoule spaced a constant distance from each other to catch the image signals of each of the photograph partitions so as to draw out a first abnormal signal as a reference with a level of sensitivity low enough to detect the foreign matter from each of the image signals of each photograph partition of the ampoule and, simultaneously, to draw out a second abnormal signal as a reference with a level of sensitivity much higher than the level to remove the minute flaws thereby to generate the sequential voltage signals, a controlling circuit for converting the first and second abnormal signals, respectively, into a logic "1" signal in the corresponding address divided into a matrix of photograph partitions, a memory apparatus for respectively temporarily storing the voltage signals of the converted logic "1", a memory apparatus for comparing the photograph partitions with each other to select a specific photograph partition including the largest number of logic "1" signals in the second abnormal signal thereby to temporarily store the voltage signals, a controlling apparatus for sequentially delivering the voltage signals stored in the memory apparatus, a logical operation circuit for drawing out the logic "1" signal of the second abnormal signal in a specific photograph partition and the first abnormal signal in each of the other photograph partitions to combine the logic "1" signals of both signals to sequentially provide the logical sum of them for each of the corresponding addresses, and thereafter performing the calculation to provide the logical exclusive OR between the logical sum and the logic "1" signal of the second abnormal signal in the specific photograph partition to generate an elimination signal when the logic "1" signal wherein both signals mutually do not have given relationship to the operation value, is provided, and a control synchronizing circuit for synchronizing the camera to the memory apparatus to send the two voltage signals to the logical operation circuit in correctly drawn out relation. This apparatus performs a method comprising the steps of passing the ampoule at almost a constant speed before the television camera provided at the fixed position within the inspection region while turning the fluid contents of the ampoule, sequentially scanning the ampoule by means of the television camera at at least three positions or more of the ampoule spaced a constant interval from each other to catch the image signals of each photograph partition, drawing out a first abnormal signal as a reference with a level of sensitivity low enough to detect the foreign matters from each of the image signals and, simultaneously, drawing out a second abnormal signal as a reference with a level of sensitivity much higher than the above-described level to get rid of the minute flaws, converting the first and second abnormal signals respectively into the logic "1" signals in the corresponding addresses divided into the matrix of photograph partitions for the temporary storage thereof, comparing the photograph partitions with each other to select a specific photograph partition including the largest number of logic "1" signals in the second abnormal signal thereby to perform the temporary storage thereof, drawing out the logic "1" signal of the second abnormal signal in the specific photograph partition and the first abnormal signal in each of the other photograph partitions from the memory apparatus while synchronizing the camera with the output of the memory apparatus, sequentially providing the logical sum for each of the corresponding addresses of the logic "1" signals of both signals, thereafter performing a logical operation of providing the logical exclusive OR of the logical sum and the logic "1" signal in the specific photograph partition, and determining that the logic "1" signal indicates the presence of the foreign matters in the fluid when the logic "1" signal comes to the digital operation value. Accordingly, the method of the present invention is higher in the practical value as an electric, automatic continuous inspection method of this type, since the foreign matter is adapted to be accurately and positively detected with low sensitivity necessary for detection except for the container flaws which can be detected with high sensitivity, and accordingly, the foreign matters of the fluid to be detected can be positively detected at a faster processing speed and with high sensitivity, having been distinguished from the minute flaws of the container, which are likely to be mistaken for and mixed up with the foreign matters if the shape of the foreign matters becomes microbic. This is because the method comprises the steps of stopping the container, turning the fluid, considering them as the images of the television camera secured to a constant position, distinguishing the minute flaws of the container as a fixed signal to be caught with the sensitivity of level higher than the sensitivity for inspecting the foreign matters, when the abnormal signal is drawn out from among the image signals to inspect the existence of the foreign matters, to remove the region of the fixed signal from a plurality of photograph partitions, and catching, as the abnormal signal of the foreign matters, only the abnormal signal, i.e., so-called floating signal caught with sensitivity, which detects the foreign matters of each photograph partition to be detected outside of the region of the fixed signal.

These and other objects and advantages of the present invention will readily be understood from the following description taken in conjunction with preferred embodiments thereof with reference to the accompanying drawings, in which:

FIG. 2 is a schematic diagram showing an ampoule inspecting method according to a first embodiment of the present invention;

Figure 3:
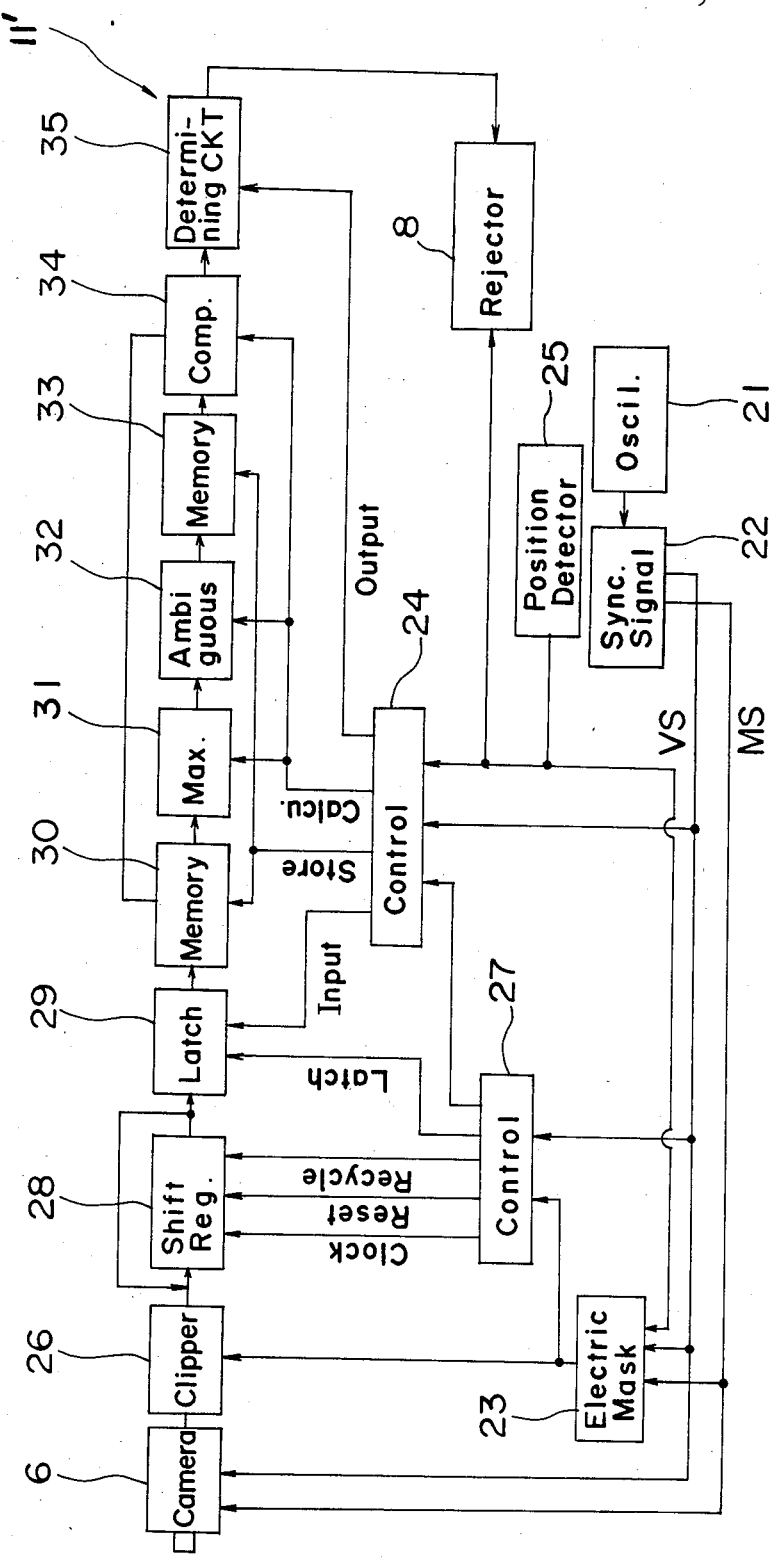
FIG. 3 is a block diagram showing the circuit of a controlling circuit according to the first embodiment of the present invention.
Figure 5:
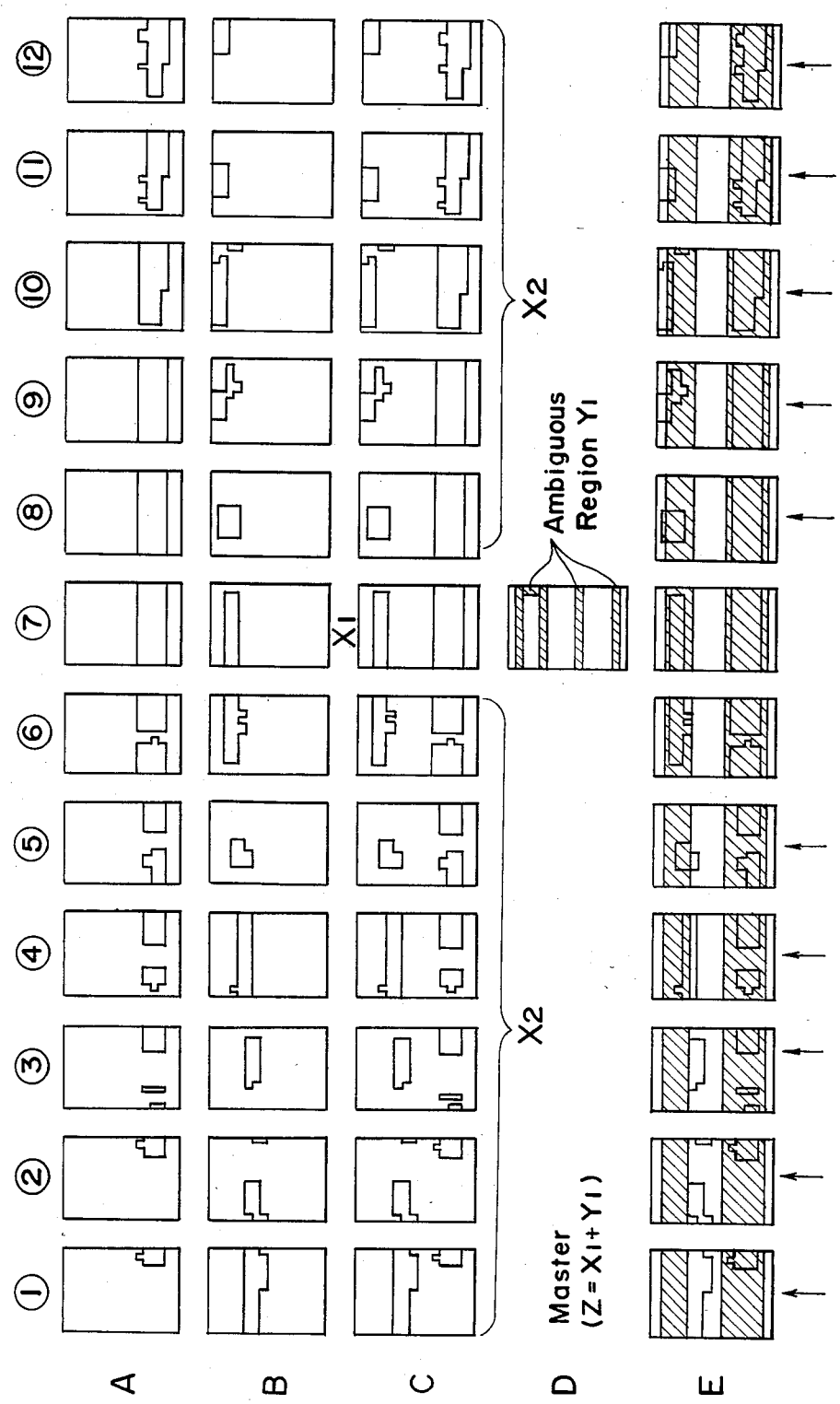
Figure 6:
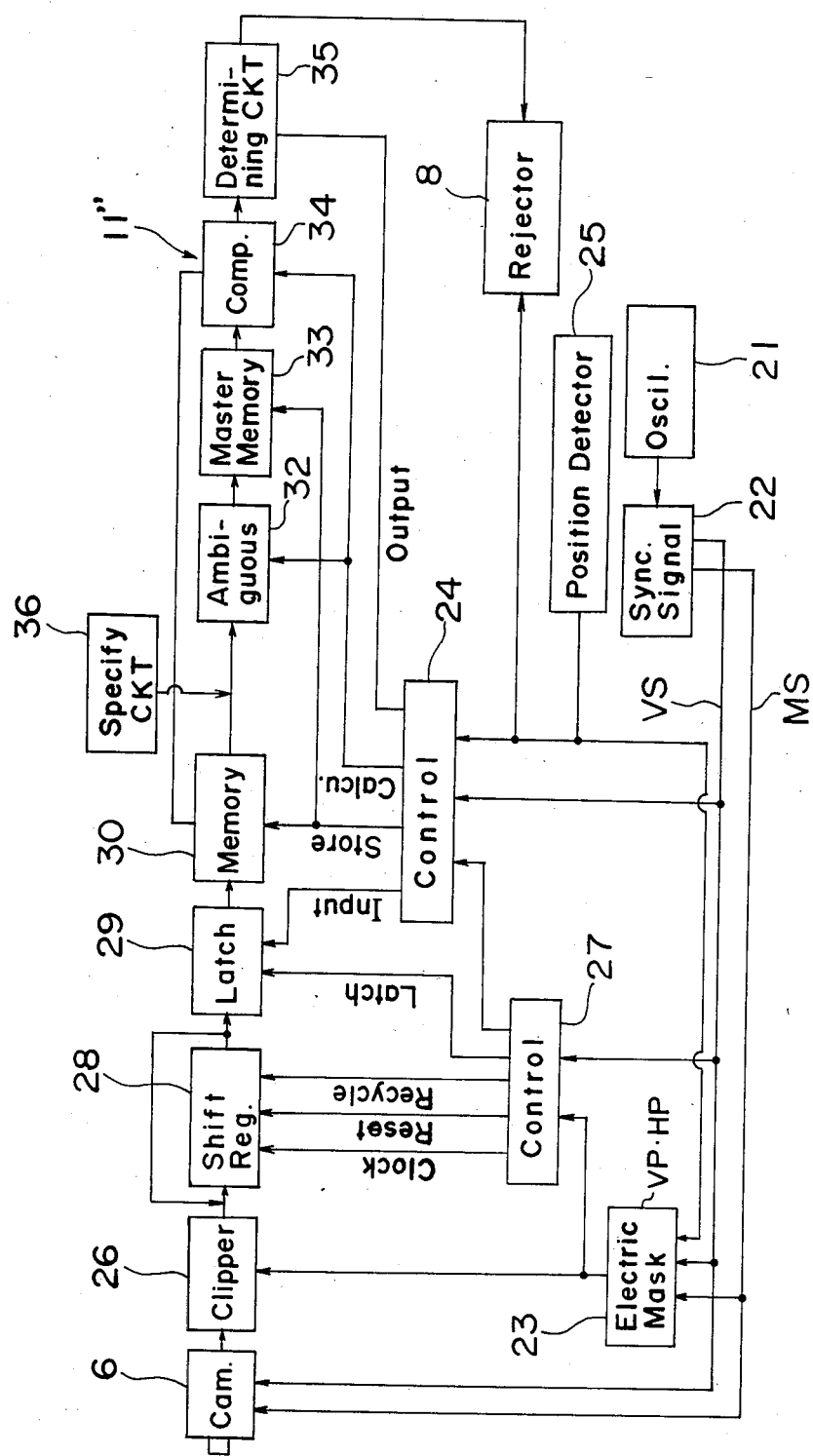
Figure 7:
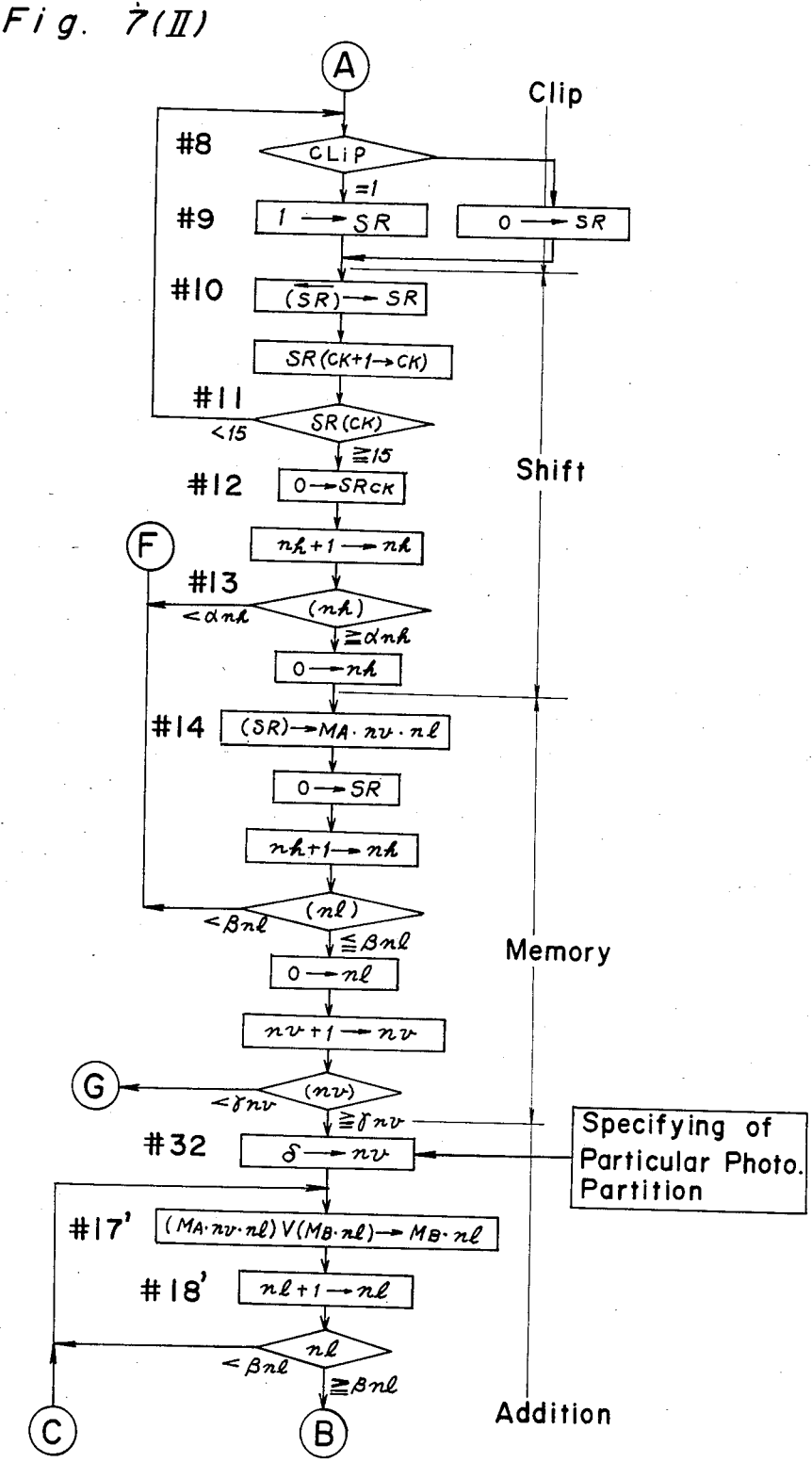
Figure 9:
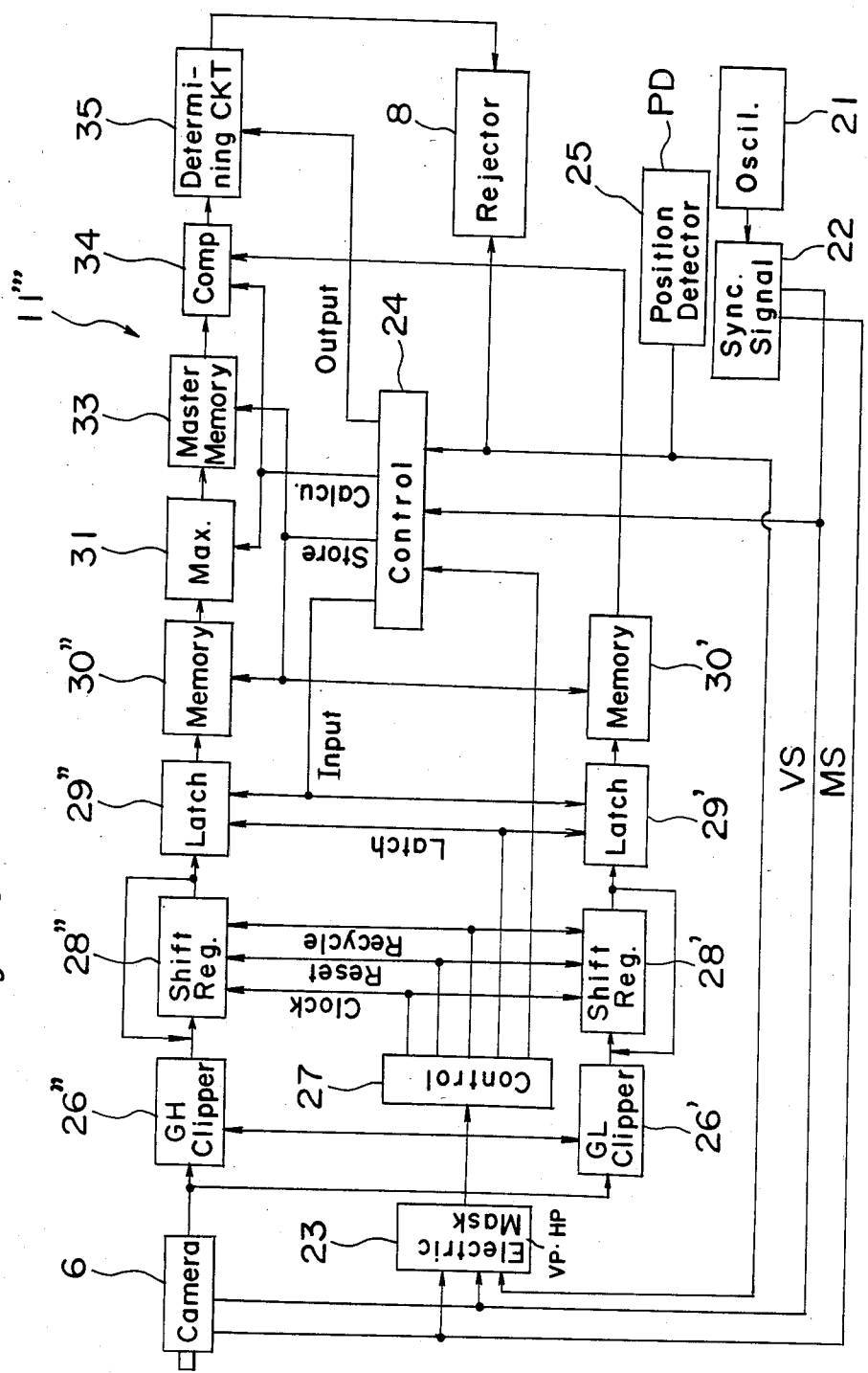
Figure 12:
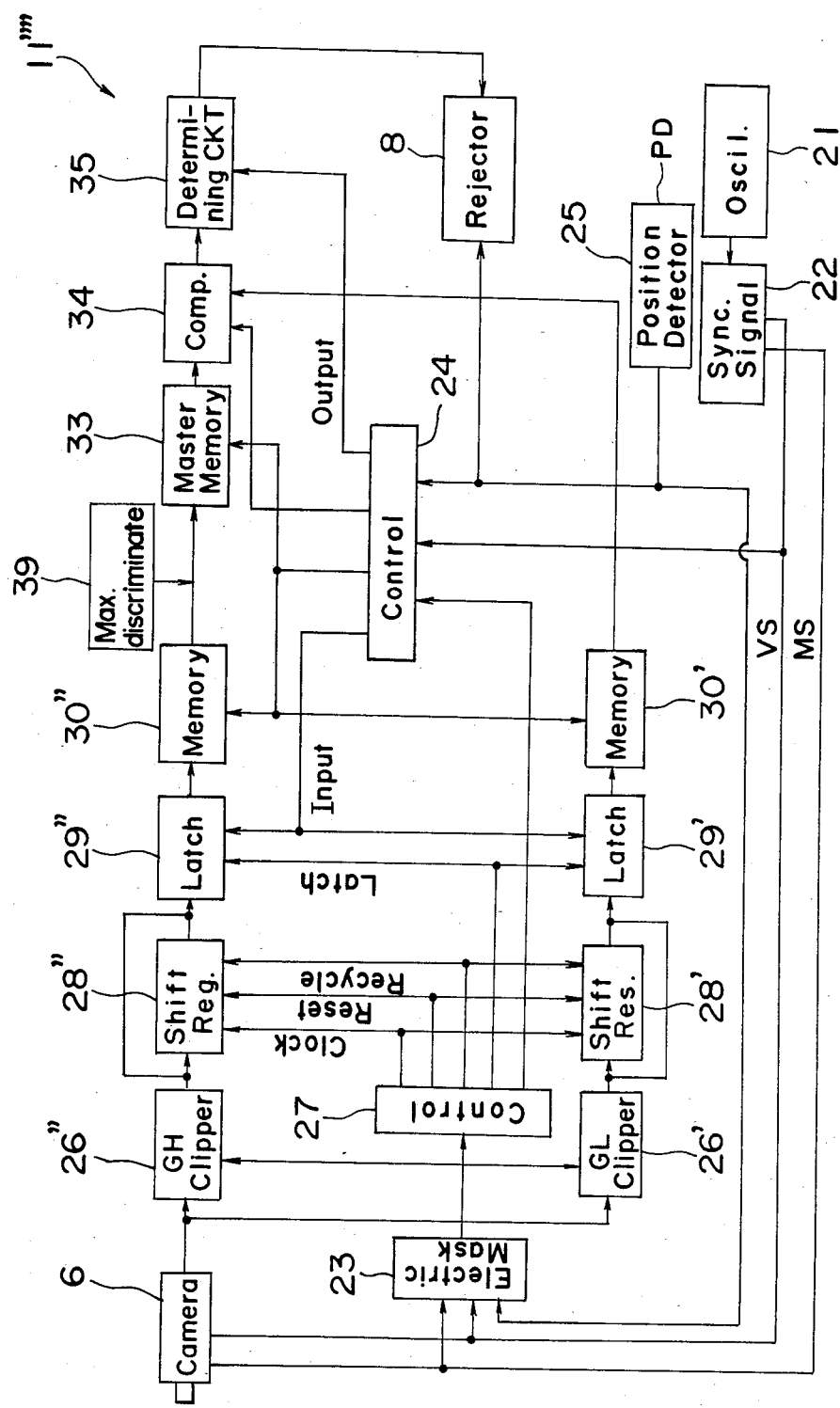
Figure 15I:
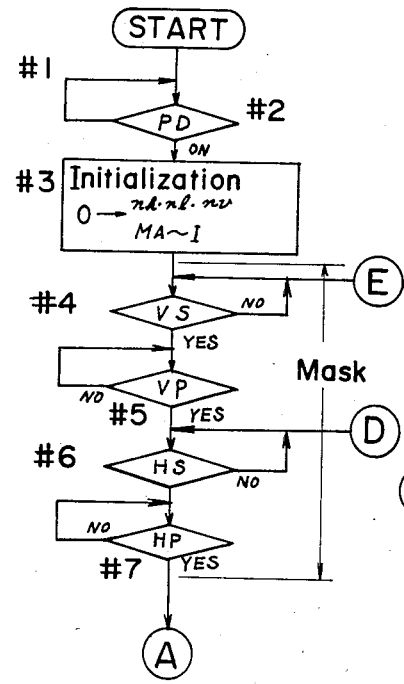
Figure 15:
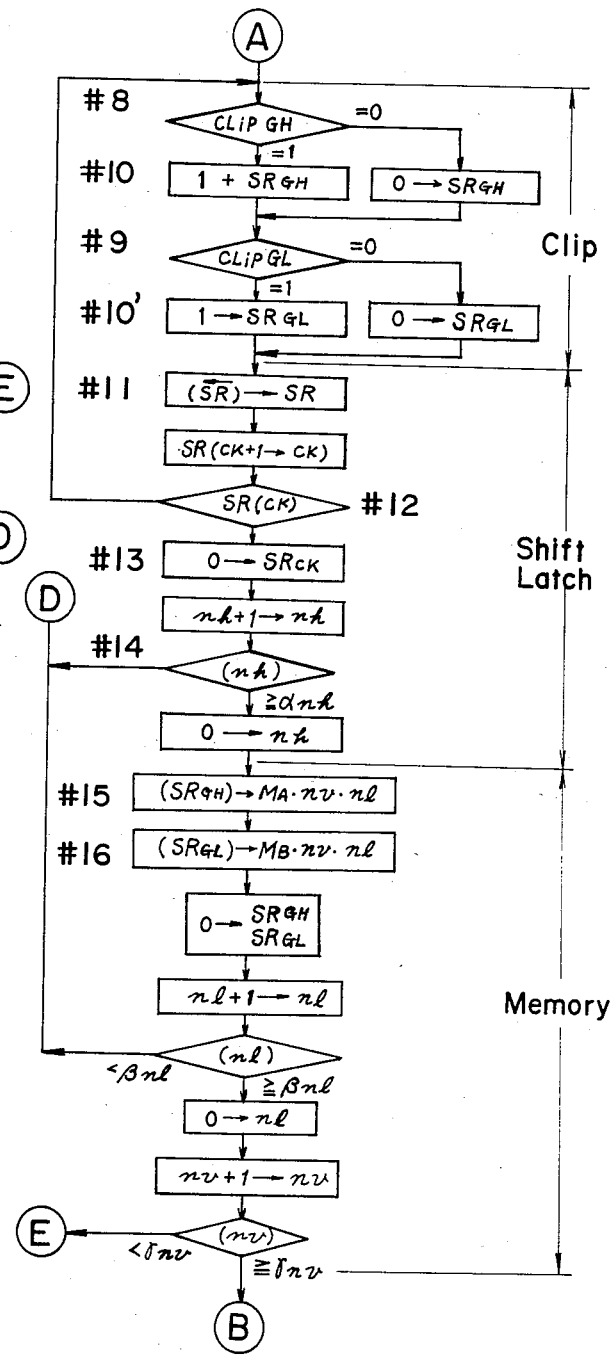

FIGS. 4(I) to 4(IV) are flow charts showing the sequence of operation of the circuit of FIG. 3;

FIG. 5 is an explanatory diagram used to explain the flow charts of FIGS. 4(I) to 4(IV);

FIG. 6 is a diagram similar to FIG. 3, showing a modified form of the controlling circuit;

FIGS. 7(I) to 7(IV) are flow charts showing the sequence of operation of the circuit of FIG. 6;

FIG. 8 is a diagram similar to FIG. 2, showing the method according to a second embodiment of the present invention;

FIG. 9 is a diagram similar to FIG. 3, showing the controlling circuit according to the second embodiment of the present invention;

FIGS. 10(I) to 10(IV) are flow charts showing the sequence of operation of the circuit of FIG. 9;

FIG. 11 is an explanatory diagram used to explain the flow charts of FIGS. 10(I) to 10(IV);

FIG. 12 is a diagram similar to FIG. 9, showing a modified form of the circuit of FIG. 9;

FIGS. 13(I) to 13(IV) are flow charts showing the sequence of operation of the circuit of FIG. 12;

FIG. 14 is a diagram similar to FIG. 9, showing a further modified form of the circuit of FIG. 9; and FIGS. 15(I) to 15(IV) are flow charts showing the sequence of operation of the circuit of FIG. 14.

The inspecting method will be fully described in connection with an apparatus for inspecting foreign matters in an ampoule with medical fluid being contained therein.

Figure 1:
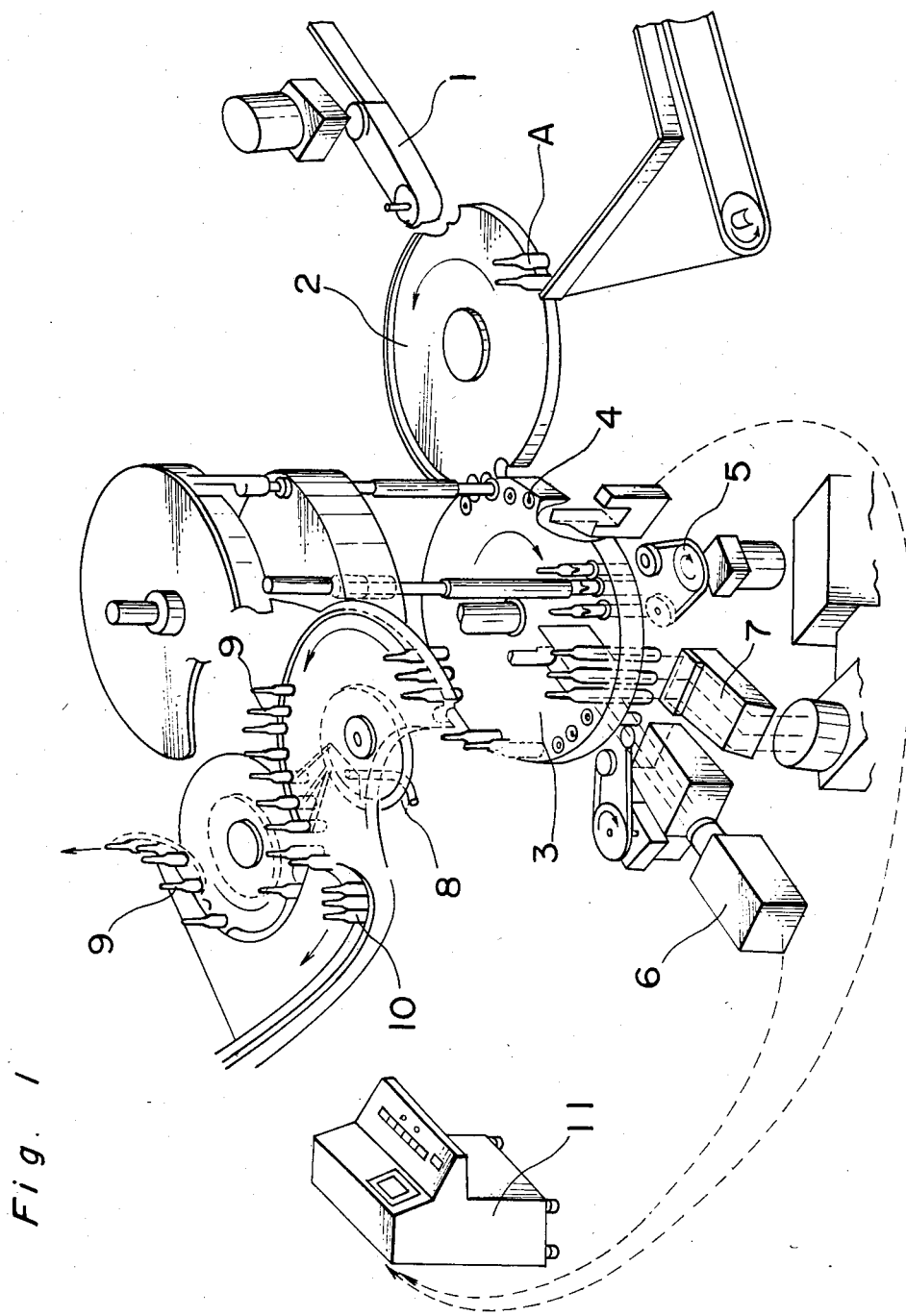
FIG. 1 is a schematic perspective view showing an automatic ampoule inspecting apparatus to which the present invention is applied.

FIG. 1 shows an apparatus for inspecting ampoules on which the method of the present invention is applied. Ampoules A each containing medical fluid therein are to be inspected about foreign matters contained in their medical fluid. The ampoules are sequentially fed one by one onto ampoule holders 4, which are disposed at equal spaces on the circular periphery of a rotary disc 3, from the supply position through a supply star-wheel 2 from a feeder 1. The rotary disc 3 is rotated clockwise at a low speed continuously at an equiangular speed, while the ampoule holder 4 provided on the constant radius is rotated at a high speed by a drive apparatus 5 around the holder shaft at a particular position thereby to spin the medical fluid contained in the ampoule A. When the ampoule A enters in an inspection region, the rotation of the ampoule holder for and, hence, the ampoule A, is stopped to allow the medical fluid within the ampoule to turn under the influence of an inertia force. At the middle of the inspection region, a television camera 6 and an illumination lamp 7 are provided at a given position in front of the rotary disc so that the entire ampoule A illuminated by the illumination lamp 7 may be photographed by a television camera 6. The picture of the television camera 6 is sufficiently large so that the entire ampoule may be photographed at least at three positions or more at given invervals as the ampoule A, together with the rotary disc, passes through the inspection region. For example, the images of the entire ampoule are photographed by the television camera at equally spaced twenty-four positions, obtained by dividing by 23 intervals a given distance leading from the initial position where one ampoule A has entered the inspection region to the final position where the ampoule A sequentially moves together with the rotary disc and is not out of the inspection region. Thus, the photographed image signals of the twenty-four partitions are provided. When the ampoule has entered the inspection region, the entire ampoule is illuminated almost uniformly at the respective photographing positions by the illumination lamp 7 so that the pictures of the ampoule A can be taken by the television camera 6. The pictures of the ampoule A are caught at each position by the television camera 6 which in turn transmits the image signals to a controlling circuit 11. The controlling circuit 11 discriminates the existence of foreign matters contained in the medical fluid, which is adapted to be relieved through the illumination, in such a procedure as described in detail hereinbelow to detect an abnormal signal when the foreign matter exists, and feeds the abnormal signal to an ampoule rejector mechanism 8. When an electromagnetic apparatus (not shown) has received the abnormal signal from the controlling circuit 11, an ampoule corresponding thereto is rejected from the passage 9 for the articles of good quality so that it may be picked up to the other unit 10 as a defective article.

The present invention is directed to the controlling circuit 11 applicable to any ampoule inspection apparatus of the type described with reference to and shown in FIG. 1. Therefore, some embodiments of the controlling circuit will now be described separately under respective headings.

FIRST EMBODIMENT (FIGS. 2 TO 7)

Referring to FIG. 2, the controlling circuit 11' undergoes a process of longitudinally and latitudinally masking off the picture faces of the image signals in each photograph partition 12 (or frame) of the ampoule A to be inspected into many small-blocks to catch abnormal signals $X_1$ in accordance with a constant reference of a clipper circuit for each of addresses of the respective image signals 13, setting the abnormal signals in image signals of a particular photograph partition and their environs, i.e., an ambiguous region $Y_1$ composed of a constant number of longitudinal, lateral, oblique blocks as a master Z, comparing the photograph partition 12Z of the master Z with the other photograph partition 12 to decide that a different type of signal is the abnormal signal, produced in a region except for the master region, from among the abnormal signals $X_2$ fetched from the image signals of the other photograph partition, and fetching the signal to enable the corresponding defective ampoule to be rejected for discriminating the quality of the ampoule.

The controlling circuit 11' which is provided between the television camera 6 and the rejector mechanism 8 is considered variable in construction. For example, the controlling circuit shown in FIG. 3 is of such a character as to operate in a manner as shown in FIG. 4. FIG. 5 shows a sequence of development wherein each of the photograph partitions is sequentially processed in accordance with the flow chart of FIG. 4.

In the controlling circuit 11' shown in FIG. 3, a clock pulse generated by a known oscillator generates a vertical synchronizing signal (VS) and a horizontal synchronizing signal (HS) through a synchronizing circuit 22 composed of a frequency divider. The signals are sent to the television camera 6, and also to an electric masking circuit 23 which receives the photograph images of an ampoule from the picture image face of the television camera 6 and makes masks as upper, lower, left, right block regions, and to a controlling apparatus 24 which synchronizes so that the controlling timing of the operations in each circuit may coincide with each other. The initial timing in the electric masking circuit 23 and the controlling apparatus 24 is performed by a detection signal of a position detector 25, which detects the position of an ampoule A in synchronized relation with the photographing operation, on the particular position of the television camera 6, of the ampoule A. The electric masking circuit 23 is composed of a string address circuit for instructing each address of a given width within left and right regions and a row address circuit for instructing each address of a given width within top and bottom regions. The address signals are sent to a shift register circuit 28, a latch circuit 29, a controlling apparatus 24 and an eliminating mechanism 8 through a clipper circuit 26 and a shift register controlling circuit 27. The controlling apparatus 24 synchronizes so that the latch circuit 29 may synchronize with its subsequently series-connected memory circuit 30, a maximum discriminating circuit 31, an ambiguous-region setting circuit 32, a master memory circuit 33, a comparing circuit 34, and a defective article discriminating circuit 35 in operating timing. Accordingly, the clipper circuit 26 of low-sensitivity level (GL) to be connected with the television camera 6 has a shift register circuit 28, a latch circuit 29 and, a memory circuit 30 connected sequentially in series therewith. And the memory circuit 30 is directly connected with a comparing circuit 34 and also is connected with the comparing circuit 34 through the maximum discriminating circuit 31, the ambiguous region setting circuit 32 and the master memory circuit 33. The comparing circuit 34 has the defective article discriminating circuit 35 and the eliminating mechanism 8 connected in series therewith.

As shown in FIG. 2, the image signals of an ampoule to be taken from the television camera 6 are considered as an electric signals at a given reference, which is sufficient in sensitivity enough to detect microparticles, wherein optical abnormal signals reflected on the image face of the television camera 6 have been preset by a clipper circuit 26. The abnormal signals in each string are shifted to each row for each address by the shift register circuit 28 and are stored at a memory circuit 30, while the abnormal signals are being sequentially latched in the latch circuit 29. The low-sensitivity clip circuit 26 has a clip level (GL) of a given sensitivity as the lowest reference required to detect foreign matters contained in the ampoule fluid from the image signals of the ampoule. When the image signal lower than this level (GL) is fed to the clip circuit 26, the output becomes 0. When an image signal higher than this level enters, the output becomes 1. Signals drawn out at the sensitivity clipper circuit 26 are latched at each of the latch circuit 29, being sequentially shifted for each address at the following shift register circuit 28. The signals are stored in the memory circuit 30 as the signals of 0.1 for each address of a matrix about each of the photograph partitions. Accordingly, the signals of 1.0 in the matrix address for each photograph partition about all the photograph partitions are stored in the memory circuit 30. For example, the signals are stored in the memory circuit 30 as a series of 0.1 signals in such a matrix as shown in FIG. 2(4). The 1 signal thereof is provided as a frame line shown for each of the photograph partitions as shown in FIG. 5. In FIG. 5, $A_1$ shows a flaw detected at the sensitivity clip circuit within the frame of 1 signal; $B_1$ shows a foreign matter detected at the sensitivity clip circuit within the frame of 1 signal; $C_1$ shows the sum of the $A_1$ and the $B_1$; $D_1$ shows a given size of ambiguous region added to the entire outer periphery of a particular photograph partition within the frame with the whole as 1 signal; and $E_1$ shows the sum of the $D_1$ and $A_1$, $B_1$. The 0, 1 signals of all the photograph partitions of the memory circuit 30 connected with the sensitivity clip circuit 26 are sent to the following maximum discriminating circuit 31 to compare the 0, 1 signals of each photograph partition with each other in the maximum discriminating circuit 31 to select one of the photograph partitions 12M, wherein the 1 signal is largest in number among all the photograph partitions, that is 0, wherein the area of the frame $X_1$ of the 1 signal as shown in FIG. 5 is maximum thereby to add a particular width of ambiguous region $Y_1$, as a particular address, to the outer periphery of each address of the 1 signal at the ambiguous region setting circuit 32, and thereafter to store all the addresses $(X_1+Y_1)$ as a master partition in the master memory circuit 33. Namely, the ambiguous region setting circuit 32 specifies a preset given peripheral address $Y_1$ to the periphery of each abnormal signal $X_1$ as 1 signal in a particular photograph partition selected in the maximum discriminating circuit 31 to temporarily store in the following matrix memory circuit 33 a master matrix region $(X_1+Y_1)$, wherein the ambiguous region address and the measured address are combined with each other as a master partition. A series of 0, 1 signals for each matrix in a master partition, which has a particular number of 1 signals stored in the master memory circuit 33 as described hereinabove are drawn out to the comparison circuit 24, while a series of 0, 1 signals for each matrix in each of the photograph partitions, through the sensitivity clip circuit 26, stored in the memory circuit 30 are directly inputted into the comparison circuit 34. A series of 0, 1 signals for each matrix in a master partition, which has a particular number of 1 signals of the master memory circuit 33 are sequentially compared with a series of 0, 1 signals for each matrix in each of the photograph partitions. If the 1 signal of the latter exists even by one outside of the frame of the 1 signal of the former, it is outputted to a defective article discriminating circuit 35, and its corresponding ampoule is taken as a defective article to the other portion 10 from the passage 9 of the good article by the rejector mechanism 8. The comparison circuit 34 compares the 1 signals for each matrix in the photograph partition, which has the 1 signal of the maximum number in the photograph partition as one master stored in the master memory circuit 33 as described hereinabove, i.e., in the photograph partition to be detected in the sensitivity clip circuit 26, with the 1 signal of a master wherein 1 signal is further added to the address in a particular width of ambiguous region in the vicinity, with the 1 signal for each matrix in each photograph partition in all the photograph partitions to be detected in the sensitivity clip circuit 26. An output signal is transmitted to the defective article discriminating circuit 35 when the 1 signal of each photograph partition of all the photograph partitions to be detected by the sensitivity clip circuit 26 exists outside the frame of the 1 signal of the master. For example, when a signal like in the first through fifth and eighth through twelfth photograph partitions among the photograph partitions of FIG. 5E exists, the output signal is transmitted to the circuit 35 to operate the defective article discriminating circuit 35.

The operation of the controlling circuit 11' of FIG. 3 as described hereinabove will be described hereinafter with reference to the flow charts of FIGS. 4(I), (II), (III) and (IV). [A] through [G] in FIGS. 4(I) to 4(IV) show the respective connection points.

First, the supply of an electric power is initiated at the stage #1 and the initial position of an ampoule to be inspected is detected by a position detector (PD) at the stage #2. Then, the initial conditions of electric mask count (nv), horizontal synchronizing signal count (nh), electric mask row-number count (n1) and electric mask row and string-number count (M) are set at the stage #3. In this case, the ampoule A is temporarily rotated and thereafter is placed on a rotary disc. Although the ampoule A itself stops at a given position, the medical fluid contained within the ampoule keeps turning due to its inertia. Accordingly, if minute flaws exist on the ampoule and unwanted micro-particles exist in the medical fluid, the flaws rotate integrally with the rotary disc 3 while the foreign matters are freely displaced within the ampoule and do not stop even for a moment. The size of the address of the matrix of the photograph partition to be sequentially photographed is determined by a vertical synchronizing signal (vs) at the stage #4. Each position signal (vp) of the vertical electric mask corresponding to the photograph partition is determined at the stage #5. Similarly, the size of the address of the matrix of the photograph partition is detected by a horizontal synchronizing signal (HS) at the stage #6. Each position signal (HP) of the horizontal electric mask corresponding to the photograph partition is detected at the stage #7. Accordingly, the photograph position for each address to be specified by the photograph range of the photograph mask 12 and the matrix is determined at the stages #5 and #7. Then, to draw out an abnormal signal on the clip at the stage #8 from the image signals, which have scanned an ampoule in the photograph mask, a Schmidt level GL is set as the lowest reference. When the scanning lines of the image signals, which have scanned the ampoule in the photograph mask, is thrown onto the clip at the stage #8, the clipping operation is performed with the signals lower than the set level in the scanning lines rendered 0 (normal), and the signals higher than the set level rendered 1 (abnormal), the 0, 1 signals for each address of the scanning lines are temporarily stored in the shift register at the stage #9. At the stage #10, the respective shift register registers the signals of the 0, 1 while shifting them at a given distance in accordance with each address of the scanning lines. At the stage #11, the signal pushed out through the shifting operation is latched. At the stage #12, the 0, 1 signals of a given number, namely, the 0, 1 signals across all the addresses about each one of the horizontal scanning lines of the the photograph mask, for example, sixteen 0, 1 signals when one time of scanning line is divided into sixteen-divided addresses, are latched. At the stage #13, the 0, 1 signals address-divided for each one-scanning line as described hereinabove are accumulated by a given number. For example, the 0, 1 signals of the sequentially continued five scanning lines are accumulated for each of the same addresses as one block, and the block is displayed as 1 when 1 exists, even if it is one in each signal of each block. The 0, 1 signals for each of the addresses detected by the low sensitivity clip at the stage #8 in a memory element (MA, nv, n1) as the 0, 1 signals of each one row are stores for each row at the stage #4. Accordingly, the 0, 1 signals (MA, nv, n1) for each address detected by the low sensitivity clip in the memory element at the stage #14 are stored in the number of all the rows constituting one partition for each photograph partition, for example, sixteen rows. All the photograph partitions, for example, twelve photograph partitions with one ampoule being photographed therein, are stored as a series. Then, the 0, 1 signals of all the photograph partitions stored by the memory element at the stage #14 are drawn out to a maximum discriminating comparison element at the stage #19 and a comparison element at the stage #27. First, as a maximum discriminating circuit 31, the 0, 1 signals (MA, nv, n1) of all the photograph partitions detected by the low sensitivity clip 26 are drawn out at the step #15 for each photograph partition. The number of the 1 signals for each one-row is counted by the counter at the stage #16 for each of the photograph partitions to obtain the total number of the 1 signals for each one-row at the stage #17. The total number of the 1 signals existing in one photograph partition is counted by the counter at the stage #18. Thereafter, the number of all the 1 signals of a first photograph partition is sequentially compared with the number of all the 1 signals of the following photograph partition by the maximum discriminating comparison elements (ME, nv) at the stages #19 and #21 to store the number of all the 1 signals of the larger photograph partition by a memory element ($M_F$MAX) at the stage #20. Then, the number of all the 1 signals of the larger photograph partition is further compared sequentially with the number of all the 1 signals of the following photograph partition. Such comparison as described hereinabove is performed one after another among all the photograph partitions by the counts of the counter (nv) at the stage #21 between the photograph partitions. The largest ($M_F$MAX) in number of all the signals included in one photograph partition of all the photograph partitions is determined and selected at the stage #19. The 0, 1 signals of each row in a particular photograph partition, which has a maximum number of the 1 signals in all the photograph partitions selected in this manner, for example, partitions which have sixty-four 1 signals in the sixth in the C of FIG. 5 and is normally called master partition, are drawn out in all the rows by the counter at the stage #22, and the 1 signal (MH n1) for each address across all the rows of the photograph partition called the particular master is fed to the ambiguous circuits at the stages #23 and #24. In the ambiguous circuits, a so-called ambiguous region ($Y_1$) is set, wherein the 1 signal is added to a specified number of address next on the left side to an address, where the 1 signal exists, of the master photograph partition, in the MG at the stage #23, for example, to a 1 address, and simultaneously the 1 signal is added to a specified number of address next on the right side to an address, where the 1 signal exists, of the master partition, in the MH at the stage #24 thereby to increase the region of the 1 signal on both sides by a specified address number. For example, when the signals of "0011, 0100, 0110" have been fed to the ambiguous circuit, the 1 signals are further added to the left, right of the 1 signal in the ambiguous circuit thereby to output the signals of "0111, 1110, 1111". Also, the 1 signals can be added to the specified address next on the top and bottom sides in the ambiguous circuits at the stages #23 and #24. The 0, 1 signals of all the addresses called master partition, wherein the region of the 1 signal is enlarged by a specified range in the ambiguous circuits, are temporarily stored for each address in the master memory element ($M_1$n1) at the stage #25. The 0, 1 signals of the master partition of the master memory element ($M_1$n1) at the stage #25 are fed into the next comparison circuit 34. As the comparison circuit 34, 0, 1 signals are drawn out in each of the addresses for each photograph partition of all the photograph partitions wherein the 0, 1 signals have been detected by the low sensitivity clip to be sequentially fed from the memory element at the stage #14 by the addition element at the stage #26, and the 0, 1 signals ($M_1$n1) for each address of the master partition, which has the largest number of 0, 1 signals, to which the 1 signal of the ambiguous region has been added, to be inputted from the master memory element at the stage #25 are added to the 0, 1 signals, for each address, of each of the drawn out photograph partitions thereby to store the 0, 1 signals ($M_J$) of the number of the partitions corresponding to the number of all the photograph partitions. Furthermore, the 0, 1 signals ($M_J$) at the stage #26 are sequentially inputted to the comparison element at the stage #27, while the 0, 1 signals ($M_1$n1), for each address, of the master partition, which has the largest number of 0, 1 signals, to which the 1 signal of the ambiguous region has been added again from the master memory element at the stage #25, are fed to the stage #27, so that they are compared with each other (exclusive OR) to determine whether the 1 signal for each address in each photograph partition for each photograph partition of all the photograph partition to be drawn out from the memory element at the stage #14 exists within each address wherein the 1 signal ($M_1$n1) in the master partition exists or the 1 signal exists outside of each address wherein the 1 signal in the master partition exists. In the comparison element at the stage #27, the 1 signal in each photograph partition at the stage #26 and the 1 signal in the master photograph partition at the stage #25 are counted across all the rows of each photograph partition, by the counter at the stage #28 for each address. The counting operation is performed across all the photograph partitions by the counter at the stage #29 for each of the photograph partitions. When the 1 signal in each photograph partition at the stage #26 stays outside the address of the 1 signal in the master partition at the stage #27, a signal is transmitted as a defective article at the stage #29 even if the 1 signal is one, to operate the rejector mechanism 8.

Accordingly, to inspect the existence of unwanted micro-particles contained in the medical fluid filled in the sealed transparent ampoule with minute flaws located therein as described hereinabove, the ampoule is caused to pass at an approximately constant speed before a television camera disposed at a fixed position within the inspection region, having turned the medical fluid in the ampoule. The container is sequentially scanned by the television camera at at least three positions or more of the ampoule placed at a given interval to catch an abnormal signal from the image signals of each photograph partition. A photograph partition with the maximum number of the abnormal signals therein is selected to set, as a master partition, the position where the abnormal signals of the photograph partition exist, and a specified master row or/and string range including its neighboring ambiguous region. The image signals of the photograph partition between the master partition and the other photograph partition are compared with each other to draw out the abnormal signal only, existing beyond the specified range of the master partition of the master photograph partition, among the abnormal signals of the other photograph partition to determine it as an unwanted micro-particles contained in the fluid contents so that only the existence of the foreign matter in the medical liquid can be detected through the separation of the ampoule flaw from the foreign matter in the medical liquid.

It is to be noted that the controlling circuit 11' can be modified in numerous way. An example of the modified circuit is shown in FIGS. 6 and 7. The controlling circuit 11" will now be described with reference to a block diagram shown in FIG. 6, and a flow chart shown in FIG. 7. In this modification, each of the photograph partitions is photographed, respectively, with a given sensitivity GL to provide the n number of photograph partitions composed of $A_1$, $A_2$, $A_3$, ... $A_{n-1}$ and $A_n$ which have detected the abnormal signals. A particular photograph partition Am is specified from the photograph partitions. A specified address is further added to the outer periphery of an address wherein the abnormal signal of the specified photograph partition exists to set a specified ambiguous region to see whether or not the foreign matters exist from the abnormal signal in the image signals of the other photograph partition except for the specified region with the specified photograph partition as a reference. Accordingly, the block diagram of FIG. 6 differs from the block diagram of FIG. 3 in that the maximum discriminating circuit 31 of FIG. 3 is removed and a maximum specifying circuit 36 is provided, instead. Namely, while in the maximum discriminating circuit 31 of FIG. 3, a master photograph partition, with the largest number of 1 signals provided therein, among all the photograph partitions is automatically selected to make a master partition wherein an ambiguous region has added to the periphery of the 1 signal to sequentially compare the 1 signal of the master partition with the number of the 1 signals of each photograph partition, the maximum specifying circuit 36 of FIG. 6 is such that a particular photograph partition is artificially specified among all the photograph partitions to add the ambiguous region to the periphery of the 1 signal of the specified photograph partition through the ambiguous specifying circuit 32 to make a master partition so that the 1 signal of the master partition may be stored in the following master memory circuit 33. To specify the particular photograph partition, an operator may specify a specific photograph partition in accordance with his experiences while monitoring all the photograph partitions by the television camera 6, or may specify, as a specific photograph partition, a photograph partition which is considered to have the largest number of 1 signals in accordance with his experiences, for example, such as located at the center among all the photograph partitions. With reference to the flow chart of FIG. 7, the steps #15 to #22 shown in FIG. 5 are removed, and all the 0, 1 signals for each address of a specific photograph partition specified at the stage #31 are drawn out from the memory element in the stage #14 into the master memory element (nv) at the stage #32. Also, all the 0, 1 signals of an addition partition specified optionally and selectively at the stage #34 to the memory element in the stage #33 are added to it, and then all the 0, 1 signals of the master memory elements in the stages #32 and #33 are adapted to be drawn out to the ambiguous elements in the stages #23 and #24. Since the other construction and operation of the modification are completely the same as those of the first embodiment, the details thereof are omitted. As described hereinabove, in the modification, the 0, 1 signals of the specified photograph partition may be drawn out by the memory element at the stage #32. Also, the other specified photograph partition may be drawn out by another memory element and added to the stage #32. Accordingly, the number of the photograph partitions to be specified may be optionally selected.

SECOND EMBODIMENT (FIGS. 8 TO 15)

As shown in FIG. 9, the controlling circuit 11''' longitudinally and latitudinally marks off, by a masking circuit, the picture faces of each photograph partition of the ampoule A to be inspected into many small-blocks to catch abnormal signals from each photograph partition 12, in accordance with the particular reference of a clipper circuit for each of addresses of a signal generated during a given period of time. The controlling circuit fetches a first abnormal signal $X_1$ with a level GL as a reference, the level GL being low in sensitivity enough to detect unwanted micro-particles from each image signal 13, and simultaneously fetches a second abnormal signal $X_2$ with a level GH as a reference, the level GH being much higher in sensitivity than the above-described level to remove the minute flaws, and compares a second abnormal signal $X_2$ of a image signals in a particular photograph partition 12M with a first abnormal signal $X_1$ in the image signals of the other photograph partition 12 to fetch the first abnormal signal $X_1'$, when the latter and the former exist in a different region of the photograph partition, to discriminate that the unwanted micro-particles are mixed in the fluid of the ampoule thereby to fetch a signal from an output circuit to permit the ampoule containing the foreign matters to be rejected.

The controlling circuit 11''' which is provided between a television camera 6 and a rejector mechanism 8 so far shown in FIG. 9 is of a type operable in a manner as shown by a flow-chart in FIG. 10. FIG. 11 shows a sequence of development wherein each of the photograph partitions 12 is sequentially processed in accordance with the flow chart of FIG. 10.

In the controlling circuit 11''' shown in FIG. 9, a clock pulse generated by a known oscillator generates a vertical synchronizing signal (VS) and a horizontal synchronizing signal (HS) through a synchronizing circuit 22 composed of a frequency divider. The signals are sent to the television camera 6, and also to an electric masking circuit 23, which receives the photograph images of an ampoule from the picture image face of the television camera 6 and makes masks as upper, lower, left, right block regions, and to a controlling apparatus 24, which synchronizing so that the controlling timing of the operations in each circuit may coincide with each other. The initial timing in the electric masking circuit 23 and the controlling apparatus 24 is performed by a detection signal of a position detector 25, which detects the position of an ampoule A in synchronized relation with the photographing operation, on the particular position of the television camera 6, of the ampoule A. The electric masking circuit 23 is composed of a string address circuit for instructing each address of a given width within left, right regions and a row address circuit for instructing each address of a given width within top and bottom regions. The address signals are sent to shift register circuits 28', 28", latch circuits 29', 29", and a controlling apparatus 24 through clipper circuits 26', 26" and shift register controlling circuit 28', 28". The clipper circuit is provided with a pair of high sensitivity clipper circuit 26" and low sensitivity clipper circuit 26'. The high sensitivity clipper circuit 26" has a shift register circuit 28", a latch circuit 29", a memory circuit 30", a maximum discriminating circuit 31 and a master memory circuit 33 connected sequentially in series therewith, while the low sensitivity clipper circuit 26' has a shift register circuit 28', a latch circuit 29' and a memory circuit 30' connected sequentially in series therewith. Finally, both are connected with a comparing circuit 34. In addition, the comparing circuit 34 has a defective article discriminating circuit 35, a rejector mechanism 8 connected therewith in series.

As shown in FIG. 9, the image signals of an ampoule to be taken from the television camera 6 are considered as electric signals at given references GH and GL of the high sensitivity and low sensitivity, wherein optical abnormal signals reflected on the image face of the television camera 6 have been preset by the clip circuits 26' and 26". The abnormal signals in each string are shifted to each row for each address by the shift register circuits 28' and 28" and are stored at the memory circuits 30' and 30" while the abnormal signals are being sequentially latched in the latch circuits 29' and 29". The low sensitivity clip circuit 26' has a low clip level of sensitivity as the lowest reference GL, which detects foreign matters contained in the ampoule fluid from the image signals of the ampoule. When the image signal lower than this level is fed, the output becomes 0. When an image signal higher than this level enters, the output becomes 1. The high sensitivity clip circuit 26" has a high clip level GH of sensitivity withih a range wherein cancellation can be made even if a flaw present in an ampoule has moved from the image signals of the ampoule, for example, about two times as high in sensitivity as the low clip level and corresponding to the level increased in sensitivity by one diaphragm stop position as compared with the low clip level GL in terms of the sensitivity of the diaphragm of the television camera 6. When an image signal lower than this level comes, the output becomes 0. When an image signal higher than this level enters, the output becomes 1. Accordingly, the image signals of an ampoule to be taken out of the television camera 6 are processed into the signals of 0 and 1 for each address at the low clip level GL of the low sensitivity clip circuit 26' and, simultaneously, are processed into the signals of 0 and 1 at the high clip level GH of the high-sensitivity clip circuit 26" for the drawing-out operation thereof. Signals drawn out at the low sensitivity clip circuit 26' and the high sensitivity clip circuit 26" are latched at each of the latch circuits 29' and 29", having been sequentially shifted for each address at the shift register circuits 28' and 28". The signals are stored in the memory circuits 30', 30" as the signals of 0 and 1 for each address of a matrix about each of the photograph partitions. Accordingly, the signals of 1 and 0 in the matrix address for each photograph partition about all the photograph partitions 12 are stored in the memory circuits 30' and 30". For example, the signals are stored in the memory circuit 30" as a series of 0 and 1 signals in such a matrix as shown in FIG. 8(4). The 1 signal thereof is provided as a frame line shown for each of the photograph partitions as shown in FIG. 11. In FIG. 11, $A_2$ shows a flaw detected at the high sensitivity clip circuit 26 as the frame of 1 signal; $B_2$ shows a foreign matter detected at the high sensitivity clip circuit 26" as the frame of 1 signal; $C_2$ shows the sum of $A_2$ and $B_2$; $D_2$ shows the flaw detected at the low sensitivity clip circuit 26' as the frame of 1 signal; $E_2$ shows a foreign matter detected at the low sensitivity clip circuit 26' as the frame of 1 signal; and $F_2$ shows the sum of $C_2$, $D_2$ and $E_2$. The 0 and 1 signals of all the photograph partitions of the memory circuit 30" connected with the high sensitivity clip circuit 26" are sent to the following maximum discriminating circuit 31 to compare the 0, 1 signals of each photograph partition with each other in the maximum discriminating circuit 31 to select one of the photograph partitions wherein the 1 signal is largest in number among all the photograph partitions, that is, the area of the frame of the 1 signal as shown in FIG. 11 is maximum, thereby to store it in the master memory circuit 33. A series of 0 and 1 signals for each matrix in a photograph partition 12M, which has the signal of a maximum number stored in the master memory circuit 33, are drawn to the comparison circuit 34. A series of signals for each matrix in each photograph partition through the low sensitivity clip circuit 26' to be fed to the comparison circuit and a series of 0 and 1 signals for each matrix in a photograph partition having 1 signal of the maximum number of the master memory circuit 33 are sequentially compared with each other in the comparison circuit 34. If the 1 signal of the former exists even by one outside the frame of the 1 signal of the latter, it is outputted to a defective article discriminating circuit 35, and the corresponding ampoule A is rejected as a defective article to the other portion 10 from the passage 9 for the ampoules by an electromagnetic device of the rejector mechanism 8. The comparison circuit 34 compares the 0 and 1 signals for each matrix in the photograph partition 12M, which has 1 signal of the maximum number in the photograph partition as one master stored in the master memory circuit 33 as described hereinabove, i.e., in the photograph partition to be detected in the high sensitivity clip circuit 26", with the 0.1 signals for each matrix in each photograph partition in all the photograph partitions to be detected in the low sensitivity clip circuit 26' stored in the memory circuit 30' connected with the low sensitivity clip circuit 26'. An output signal is transmitted when the 1 signal exists outside the frame of the 1 signal of the photograph partition 12M of one master selected through the detection in the high sensitivity clip circuit 26" among all the photograph partitions to be detected in the low sensitivity clip circuit 26'. For example, when a signal like in the third, fifth and seventh photograph partition among the photograph partitions of FIG. 11F exists, an output signal is transmitted to operate the defective article discriminating circuit 35. The operation of the controlling circuit 11 of FIG. 9 as described hereinabove will be described hereinafter with reference to the flow chart of FIGS. 4(I), (II), (III) and (IV). [A] through [F] in FIGS. 4(I) to 4(IV) show the respective connection points.

First, the supply of an electric power is initiated at the stage #1 and the initial position of an ampoule to be inspected is detected by a position detector (PD) at the stage #2. Then, the initial conditions of electric mask count (nv), horizontal synchronizing signal count (nh), electric mask row-number count (nl) and electric mask row and string-number count (M) are set at the stage #3. In this case, the ampoule A is temporarily rotated and thereafter is placed on a rotary disc. Although the ampoule A itself stops at a given position, the medical fluid contained within the ampoule keeps turning due to its inertia. Accordingly, if minute flaws exist on the ampoule and unwanted micro-particles exist in the medical fluid, the flaws rotate integrally with the rotary disc 3 while the foreign matters are freely displaced within the ampoule and do not stop even for a moment. The size of the address of the matrix of the photograph partition to be sequentially photographed is determined by a vertical synchronizing signal (vs) at the stage #4. Each position signal (VP) of the vertical electric mask corresponding to the photograph partition is determined at the stage #7. Similarly, the size of the address of the matrix of the photograph partition is detected by a horizontal synchronizing signal (HS) at the stage #6. Each partition signal (HP) of the horizontal electric mask corresponding to the photograph partition is detected at the stage #7. Accordingly, the photograph position for each address to be specified by the photograph range of the photograph mask 12 and the matrix is determined at the stages #5 and #7. Then, a Schmidt level (GH) of high sensitivity is set in advance on the clip at the stage #8 as a given level signal level required to draw out an abnormal signal from the image signals, which have scanned an ampoule in the photograph mask. A Schmidt level GL as the lowest reference which is lower in sensitivity than it and is adapted to detect the foreign matters in the ampoule fluid is set on the clip at the stage #9. When the scanning lines of the image signal, which have scanned the ampoule in the photograph mask, is thrown onto the clip at the stage #8, the clipping operation is performed with the signals lower than the set level in the scanning lines rendered 0 (normal), and the signals higher than the set level rendered 1 (abnormal), the 0 and 1 signals for each address of the scanning lines are temporarily stored in the shift register (SR) at the stage #10. When the scanning lines of the image signals which have scanned the ampoule in the photograph mask are thrown onto the clip at the stage #8, the clipping operation is performed with the signals lower than the set level in the scanning lines rendered 0 (normal), and the signals higher than the set level rendered 1 (abnormal), the 0 and 1 signals for each address of the scanning lines are temporarily stored in the shift register SR at the stage #10'. At the stages #11 and #11', the respective shift registers register the signals of 0 and 1 while shifting them at a given distance in accordance with each address of the scanning lines. At the stages #12 and #12', the signals pushed out through the shifting operation are latched. At the stages #13 and #13', the 0, 1 signals of a given number, namely, the 0, 1 signals across all the addresses about each one of the horizontal scanning lines of the photograph mask, for example, sixteen 0 and 1 signals when one time of scanning line is divided into sixteen-divided addresses are adapted to be latched. At the stage #14, the 0 and 1 signals address-divided for each one-scanning line as described hereinabove are accumulated by a given number. For example, the 0 and 1 signals of the sequentially continued five scanning lines are accumulated for each of the same addresses as one block, and the block is displayed as 1 when 1 exists, even if it is one, in each signal of each block. The 0 and 1 signals for each of the addresses detected by the high sensitivity clip at the stage #8 in a memory element (SRGH) at the stage #15 as the 0 and 1 signals of each one row are stored for each row and simultaneously, the 0, 1 signals for each address detected by the low-sensitivity clip at the stage #9 in the memory element (SRGL) at the stage #16 are adapted to be stored for each row. In the memory elements, at the stages #15 and #16, according to the former, the 0 and 1 signals (MA, nv, n1) for each address detected by the high sensitivity clip GH, and according to the latter, the 0 and 1 signals (MB, nv, n1) for each address detected by the low sensitivity clip GL, are respectively stored in the number of all the rows, for example, sixteen rows constituting one partition 12 for each photograph partition. And all the photograph partitions, for example, twelve photograph partitions, with one ampoule being photographed therein are stored as a series. Then, as a maximum discriminating circuit 31, the 0 and 1 signals (MA, nv, n1) of all the photograph partitions detected by the high sensitivity clip 26" are drawn out at the stage #17 for each photograph partition. The number of the 1 signals for each row is counted by the counter (ME) at the stage #18 for each of the photograph partitions to obtain the total number of the 1 signals for each row at the stage #19 (MF, nv). The total number of the 1 signals existing in one photograph partition is counted by the counter (n1) at the stage #20. Thereafter, the number of all the 1 signals of the first photograph partition is sequentially compared with the number of all the 1 signals of the following photograph partition by the comparison element (MG-MF, nv) at the stage #21 to store the number of all the 1 signals of the larger photograph partition by a memory element ($M_F$MAX) at the stage #22. Then, the number of all the 1 signals of the larger photograph partition is further compared sequentially with the number of all the 1 signals of the following photograph partition. Such comparison as described hereinabove is performed one after another among all the photograph partitions by the count of the counter nv at the stage #23 between the photograph partitions. The largest ($M_F$MAX) in number of all the 1 signals included in one photograph partition of all the photograph partitions is determined and selected at the stage #21. The 0 and 1 signals of each row in a particular photograph partition 12M, which has a maximum number of the 1 signals in all the photograph partitions selected in this manner, for example, a partition which has sixty-four 1 signals in the sixth in the C of FIG. 11 and is normally called master partition, are drawn out in all the rows by the counter at the stage #24, and the 0 and 1 signals (MH n1) for each address across all the rows of the photograph partition called the particular master are drawn out into the memory element at the stage #25. The 0 and 1 signals (MH n1) across all the rows of the particular master photograph partition, which includes the largest number of 0 and 1 signals, detected by the high sensitivity clip are stored for each address in the memory element at the stage #25. The 0 and 1 signals (MB, nv, n1) across the respective rows for each photograph partition in all the photograph partitions where the 0 and 1 signals have been detected by the low sensitivity clip are stored for each address in the memory element at the stage #16. As the comparison circuit 37, the 0 and 1 signals are drawn out in each of the addresses for each photograph partition of all the photograph partitions wherein the 0 and 1 signals have been detected by the low sensitivity clip 26' to be sequentially inputted from the memory element at the stage #16 by the addition element in the stage #26, and the 0 and 1 signals (MH n1) for each address of the master photograph partition, which has the largest number of 0 and 1 signals, detected by the high sensitivity clip 26" to be inputted from the memory element at the stage #25 are added to the 0 and 1 signals, for each address, of each of the drawn out photograph partitions thereby to store the 0 and 1 signals ($M_I$) of the number of the partitions corresponding to the number of all the photograph partitions. Furthermore, the 0 and 1 signals ($M_I$) at the stage #26 are sequentially inputted to the comparison element ($M_I \oplus$ MH, n1) at the stage #27, while the 0 and 1 signals (MH n1) for each address of the master photograph partition, which has the largest number of 0 and 1 signals, detected by the high sensitivity clip again from the memory element at the stage #25 are inputted to the stage #26 so that they are compared with each other (exclusive OR) to determine whether the 1 signal for each address in each photograph partition for each photograph partition of all the photograph partitions to be drawn out from the memory element at the stage #16 exists within each address wherein the 1 signal (MH n1) in the master photograph partition exists, or the 1 signals exists in the address outside each address wherein the 1 signal in the master photograph partition exists. In the comparison element, at the stage #27, the 1 signal in each photograph partition at the stage #26 and the 1 signal in the master photograph partition at the stage #25 are counted across all the rows of each photograph partition by the counter at the stage #28, for each address. The counting operation is performed across all the photograph partitions by the counter at the stage #29 for each of the photograph partitions. When the 1 signal in each photograph partition in the stage #16 stays outside the address of the 1 signal in the master photograph partition at the stage #27, a signal is transmitted as a defective article at the stage #30 even if the 1 signal is one, to operate the rejector mechanism 8.

Accordingly, to inspect the existence of unwanted micro-particles contained in the medical fluid filled in the sealed transparent ampoule with minute flaws located therein as described hereinabove, the ampoule is caused to pass at an approximately constant speed before a television camera disposed at a fixed position within the inspection region, having turned the medical fluid in the ampoule. The container is sequentially scanned by the television camera at least three positions or more of the ampoule placed at a given interval to catch an abnormal signal from the image signals of each photograph partition respectively by a low-sensitivity level GL sufficient enough to detect the unwanted micro-particles and by a high sensitivity level GH which can contain the minute flaws much higher in sensitivity than the low sensitivity level thereby to select the largest number of foreign-matter signals in the high sensitivity level of the latter. When the foreign-matter signals in each of the photograph partitions caught at the low sensitivity level of the former exist outside the arrangement of the foreign-matter signal in the selected foreign-matter signals, the signals are processed in the logical circuit 11 so that only the signal can be drawn out. Only the signal is drawn out as the abnormal signal to determine it as the unwanted micro-particle contained in the fluid contents so that only the existence of the medical-fluid foreign matter can be detected through the separation of the ampoule flow from the medical-fluid foreign matter.

It is to be noted that the controlling circuit 11''' can be modified in several ways. Two examples of the modifications of the second embodiment will now be described with reference to FIGS. 12 to 13 and FIGS. 14 and 15, respectively.

Referring first to FIG. 12, the controlling circuit 11'''' operates in a manner as shown in a flow chart shown in FIG. 13. In this modification, each of the photograph partitions is photographed, respectively, with the high and low sensitivities to provide the n number of photograph partitions composed of $A_1, A_2, A_3, \ldots A_{n-1}$ and $A_n$ photographed with the high sensitivity, and the n number of photograph partitions composed of $a_1, a_2, a_3, \ldots a_{n-1}$ and $a_n$ photographed with the low sensitivity, a particular photograph partition is optionally specified from among photograph partitions Am to compare the abnormal signal of the particular photograph partition with the abnormal signal of the other photograph partition thereby to see whether or not the foreign matters exist. Accordingly, the block diagram of FIG. 12 differs from the block diagram of FIG. 9 in that the maximum discriminating circuit 31 of FIG. 9 is replaced with a maximum specifying circuit 39. Namely, in the defective article discriminating circuit 35 of FIG. 9, a master photograph partition, with the largest number of 1 signals provided therein, among all the photograph partitions is automatically selected through the sequential comparison with the number of the 1 signals of each photograph partition. However, in the maximum specifying circuit 39 of FIG. 12, a particular photograph partition 12R is artificially specified among all the photograph partitions so that it may be stored in the following master memory circuit 33. To specify the particular photograph partition 12R, an operator may specify a specific photograph partition in accordance with this experiences, monitoring all the photograph partitions by the television camera 6, or may specify, as a specific photograph partition, a photograph partition which is considered to have the largest number of 1 signals in accordance with his experiences, for example, such as located at the center among all the photograph partitions. With reference to the flow chart of FIG. 13, the stages #17 to #25 of FIG. 10 are removed, and all the 0 and 1 signals detected by the high sensitivity clip GH for each address of a specific photograph partition specified at the step #32 are drawn out from the memory circuit in the stage #15 into the master memory element (MG n1) at the stage #31. Then, all the 0 and 1 signals of the master memory elements in the stage #31 are adapted to be inputted into the addition element apparatus in the stage #26 and the comparison element apparatus in the stage #27.

Since the other construction and operation of the modification of the second embodiment are completely the same as those of the second embodiment, the details thereof are omitted. In the modification of FIGS. 8 to 13, one photograph partition is optionally selected. A plurality of photograph partitions such as initial, middle, final photograph partitions may be optionally selected to artificially compose them to provide one photograph partition.

The further modified form of the controlling circuit according to the second embodiment of the present invention will now be described with reference to FIGS. 14 and 15.

The modification shown in FIGS. 14 and 15 differs from that shown in that the maximum specifying circuit 39 shown in FIG. 12 is removed and a circuit including a specifying circuit 40 and an ambiquous region setting circuit 41 is used, instead and also in that a reinspection determining circuit 42 including a defective determining VD number circuit 43, a detected bit counting circuit 44 and a detected bit discriminating circuit 45 is connected in parallel with the defective article discriminating circuit 35. As is the case with the maximum specifying circuit shown in FIG. 6, the specifying circuit 40 serves to artificially specify and select a particular one of the photograph partitions 12R. The image of the particular photograph partition so specified and so selected is fed to the ambiquous region setting circuit 41 whereat it is shifted bit by bit in the leftward and rightward directions, respectively, by shifting circuits 46 and 47 and is in turn OR-synthesized by an OR synthesizing circuit 48, so that the abnormal signal which has been included in the particular photograph partition and which is enlarged by one bit leftwards and rightwards can be rendered a master to be subsequently stored in the master memory 33. Referring to the flow chart shown in FIG. 15, it will readily be seen that one-bit rightward rotated shift element #42 and one-bit leftward rotated shift element #41 are provided in addition to the particular photograph partition specifying circuit #30, #32 and the master memory element #31 (Mc n1) and the synthesis ($M_F$ n1) thereof is performed by the OR synthesizing element #43 which is in turn fed to an adder #26 and a comparison element #27.

Referring to FIG. 14, the reinspection determining circuit 42 serves, as is the case with the defective article determining circuit 35, to separate a defective ampoule from acceptable ampoules in the event that the reinspection is to be required, and to cause the rejector mechanism 8 to reject the defective ampoule. The comparison circuit 34 includes an OR synthesizing circuit 49 and a comparator 50 and is operable in such a manner that outputs from the master memory circuit 33 and the GL memory circuit 30' can be OR-synthesized in the OR synthesizing circuit 49 and the output from the OR synthesizing circuit 49 is in turn subtracted by the output from the master memory circuit 33 in the comparator 50 to determine whether or not the particular photograph partition represents the presence or absence of the foreign matter in the corresponding ampoule. The number of the photographic partitions which have been determined as representing the presence of foreign matters is counted by the counting circuit 43 and, if the number of the photographic partitions so counted is greater than the specified number (x), the corresponding ampoule is determined defective, but if it is smaller than the specified number (x) and is not zero, the reinspection determining circuit 42 is activated to cause the rejector mechanism 8 (or recheck-means) to operate. In this case, only when the number of the photograph partitions is found to be zero, the corresponding ampoule is determined acceptable. It is to be noted that the reinspection determining circuit 42 is adapted to be activated to determine that all of the ampoules including the acceptable ones which have been reinspected are those reinspected, in the event that the number of bits counted by the counting circuit 44, which bits indicate that the photograph partitions stored in the master memory circuit 33 represent the presence of the foreign matters, is determined by the bit discriminating circuit 45 to be greater than the specified number (y) (y=δ2). This is for the purpose that, in the event that the master photograph partitions are inaccurate in precision, all of the corresponding ampoules can be regarded as those to be reinspected. Referring to the flow chart of FIG. 15, the number of the minute flows or foreign matters in the master photograph partitions is counted by an adding element at the stage #44, the defective ampoules are found by a first comparison element in view of the specified number (x=δ1) at the subsequent stage #45 ($M_H$), and the acceptable ampoules are found by a second comparison element at the stage #46 in view of the specified number (y=δ2), the ampoules other than that ($M_H \geq \delta1$, $M_I \geq \delta2$, and $M_H=0$) being determined as those required to be reinspected.

It is to be noted that the construction and operation of the circuit other than that described are identical with those described and shown in connection with the first mentioned modification of the circuit according to the second embodiment of the present invention, and, therefore, the details thereof are herein omitted for the sake of brevity.

What is claimed is:

1. A method of inspecting the existence of foreign matter contained in fluid filled in a sealed container having a flaw, which comprises the steps of passing said container at an approximately constant speed before a television camera provided at a stationary position within an inspection region while the fluid in the container is turned; scanning the container by the use of said television camera sequentially at at least three positions of said container spaced at a given interval such that image signals each corresponding to a photograph partition are generated at each position and such that an abnormal signal is detected from among image signals of each of the photograph partitions; setting a specified range where the abnormal signal in the image signals of a specific photograph partition has been transmitted for removing the flaw; and comparing the image signal of the particular photographic partition with the image signal of another photographic partition such that, when the abnormal signal in the image signals of another photograph partition exists beyond the specified range of said specific photograph partition, the presence of the foreign matter in the liquid within the container can be indicated by such an abnormal signal.

2. A method as claimed in claim 1, wherein said specified range includes the vicinity of the specified position at which the abnormal signal is generated.

3. A method as claimed in claim 2, further comprising the step of comparing the particular photograph partition to a photograph partition wherein the maximum number of the abnormal signals are included in the image signals through comparison of the picture signals of all the photograph partitions with each other.

4. A method as claimed in claim 2, further comprising the step of comparing said particular photograph partition to one photograph partition optionally selected from among all the photograph partitions or to the composite partition of at least two photograph partitions optionally selected.

5. A method as claimed in claim 2, further comprising the step of comparing said particular range to said specified position and the specified range wherein the entire outer periphery thereof is surrounded by a given size value.

6. A method as claimed in claim 1, further comprising the step of determining whether or not the ampoules which have been inspected are reinspected.

7. A method of inspecting the existence of foreign matter contained in fluid filled in a sealed container having a flaw, which comprises the steps of passing said container at an approximately constant speed before a television camera provided at a stationary position within an inspection region while turning the fluid contents in the container; scanning the container by the use of said television camera sequentially at at least three positions of said container, each of said three positions being spaced at a given interval such that image signals each corresponding to a photographic partition are generated at each position; fetching a first abnormal signal from said image signals with a first level which is used as a reference, said level being low enough in sensitivity to detect the foreign matter from each of said image signals and, simultaneously, fetching a second abnormal signal from said image signals with a second level which is used as a reference, said level being higher in sensitivity than said first level by an amount which is enough to remove the flaw; and comparing the second abnormal signal of the image signals in a particular photograph partition with the first abnormal signal in the image signals of another photograph partition so as to have said first abnormal signal determine that the foreign matter exists in the fluid when the latter and the former are in the different regions of the photograph partition.

8. A method as claimed in claim 7, further comprising the step of comparing said particular photograph partition to a photograph partition wherein the maximum number of second abnormal signals are included in the image signals through the comparison of the image signals of all the photograph partitions with each other.

9. A method as claimed in claim 7, further comprising the step of comparing said particular photograph partition to one optionally selected photograph partition from among all of the photograph partitions or to the composite partition of two or more photograph partitions which have been optionally selected.

10. A method as claimed in claim 7, wherein the second level is higher than the first level by a value corresponding to one stop position of a diaphragm used in the television camera.

11. A method as claimed in claim 7, further comprising the step of determining whether or not the ampoules which have been inspected are reinspected.

12. A method of inspecting the existence of foreign matter contained in fluid filled in a sealed container having a flaw, which comprises the steps of passing said container at an approximately constant speed before a television camera provided at a stationary position within an inspection region while turning the fluid contents in the container; scanning the container by the use of said television camera sequentially at at least three positions of said container, each of said three positions being spaced at a given interval such that image signals each corresponding to a photographic partition are generated at each position; fetching a first abnormal signal from said image signals with a first level as a reference, which level is low enough in sensitivity to detect the foreign matter from each of said image signals and, simultaneously, fetching a second abnormal signal from said image signals with a second level which is used as a reference, said level being higher in sensitivity than said first level by an amount which is enough to remove the flaw; setting a specified range including a specified position, and its vicinity, at which the second abnormal signals are generated; and comparing the specified range with the first abnormal signal in the image signals of another photograph partition so as to have the first abnormal signal determine that the foreign matter exists in the fluid when the latter and the former are in the different regions of the photograph partition.

13. A method as claimed in claim 12, further comprising the step of comparing said particular range to said specified position and the specified range wherein the entire outer periphery thereof is surrounded by a given size.

14. A method as claimed in claim 12, further comprising the step of comparing the particular photograph partition to a photograph partition wherein the maximum number of second abnormal signals are included in the image signals through the comparison of the image signals of all the photograph partitions with each other.

15. A method as claimed in claim 12, further comprising the step of comparing said particular photograph partition to one photograph partition which has been optionally selected from among all of the photograph partitions or to the composite partition of two or more optionally selected photograph partitions.

16. A method as claimed in claim 12, wherein the second level is higher than the first level by a value corresponding to one stop position of a diaphragm used in the television camera.

17. A method as claimed in claim 12, further comprising the step of determining whether or not the ampoules which have been inspected are reinspected.

* * * * *